(12) United States Patent
Walters

(10) Patent No.: US 6,491,187 B2
(45) Date of Patent: Dec. 10, 2002

(54) INVERTED AEROSOL DISPENSER

(75) Inventor: Peter J. Walters, Barrington, IL (US)

(73) Assignee: Seaquist Perfect Dispensing Foreign, Inc., Cary, IL (US)

( * ) Notice: Subject to any disclaimer, the term of this patent is extended or adjusted under 35 U.S.C. 154(b) by 0 days.

(21) Appl. No.: 09/776,209

(22) Filed: Feb. 2, 2001

(65) Prior Publication Data

US 2001/0023877 A1 Sep. 27, 2001

Related U.S. Application Data

(60) Provisional application No. 60/179,792, filed on Feb. 2, 2000.

(51) Int. Cl.[7] .................................................. B67D 5/06
(52) U.S. Cl. ..................... 222/185.1; 222/173; 222/182; 222/402.21; 222/402.23
(58) Field of Search ........................... 222/402.13, 184, 222/186, 185.1, 182, 173, 402.21, 402.22, 402.23

(56) References Cited

U.S. PATENT DOCUMENTS

| | | | |
|---|---|---|---|
| 1,265,177 A | * | 5/1918 | Coleman |
| 2,765,959 A | * | 9/1956 | Elliott |
| 2,821,048 A | * | 1/1958 | Efford et al. ...................... 47/1 |
| 2,910,391 A | * | 10/1959 | Toulmin, Jr. .................. 134/25 |
| 2,935,232 A | * | 5/1960 | Thomas ....................... 222/162 |
| 3,003,662 A | | 10/1961 | Meshberg |
| 3,039,659 A | * | 6/1962 | Sagarin ....................... 222/182 |
| 3,272,392 A | * | 9/1966 | Meshberg |
| 3,618,827 A | * | 11/1971 | Melocchi ..................... 222/182 |
| 3,759,431 A | * | 9/1973 | Vos |
| 3,887,115 A | * | 6/1975 | Petterson ................ 222/402.13 |
| 3,888,392 A | * | 6/1975 | Van Coney .................. 222/108 |
| 3,893,596 A | * | 7/1975 | Beres et al. ............ 222/402.19 |
| 3,979,163 A | | 9/1976 | Beard |
| 4,117,958 A | * | 10/1978 | Spitzer et al. ......... 222/402.18 |
| 4,186,853 A | * | 2/1980 | White ......................... 222/182 |
| 4,328,911 A | * | 5/1982 | Knickerbocker ............ 222/182 |
| 4,378,081 A | * | 3/1983 | van Lit .................. 222/402.13 |
| 4,416,398 A | * | 11/1983 | Knickerbocker ....... 222/402.13 |
| 4,416,399 A | * | 11/1983 | Parr et al. .............. 222/402.13 |
| 4,426,025 A | * | 1/1984 | Knickerbocker ............ 222/182 |
| D293,213 S | | 12/1987 | Crapser |
| D293,214 S | | 12/1987 | Crapser |
| 5,263,616 A | * | 11/1993 | Ablanalp ................ 222/402.13 |
| 5,335,832 A | * | 8/1994 | de Laforcade ......... 222/402.13 |
| 5,385,272 A | * | 1/1995 | Aoun |
| 5,791,524 A | * | 8/1998 | Demarest ............... 222/153.06 |
| 5,957,336 A | * | 9/1999 | Radassao et al. |
| 6,010,042 A | * | 1/2000 | Boucher et al. |

FOREIGN PATENT DOCUMENTS

| | | | | |
|---|---|---|---|---|
| EP | 2031525 A | * | 4/1980 | ........... B65D/83/14 |
| EP | 2238580 A | * | 6/1991 | ........... B65D/83/22 |
| WO | WO98/38881 | | 9/1998 | |

* cited by examiner

Primary Examiner—Leslie D. Morris
Assistant Examiner—F. Nicolas
(74) Attorney, Agent, or Firm—Frijouf, Rust & Pyle

(57) ABSTRACT

An inverted aerosol dispensing device is disclosed comprising an aerosol container extending between a top portion and a bottom portion for containing an aerosol product and an aerosol propellant therein. An aerosol valve is located at the bottom portion of the aerosol container. The aerosol valve has a valve stem for displacing the aerosol valve from a biased closed position to an open position to discharge the aerosol product from the valve stem. An undercap is secured to the bottom portion of the aerosol container for supporting the aerosol container on a supporting surface. An actuator is movably mounted relative to the undercap for moving the valve stem upon displacement of the actuator for discharging the aerosol product from the valve stem in a generally downwardly direction through the undercap. The invention is particularly useful in the dispensing of viscous aerosol products.

34 Claims, 28 Drawing Sheets

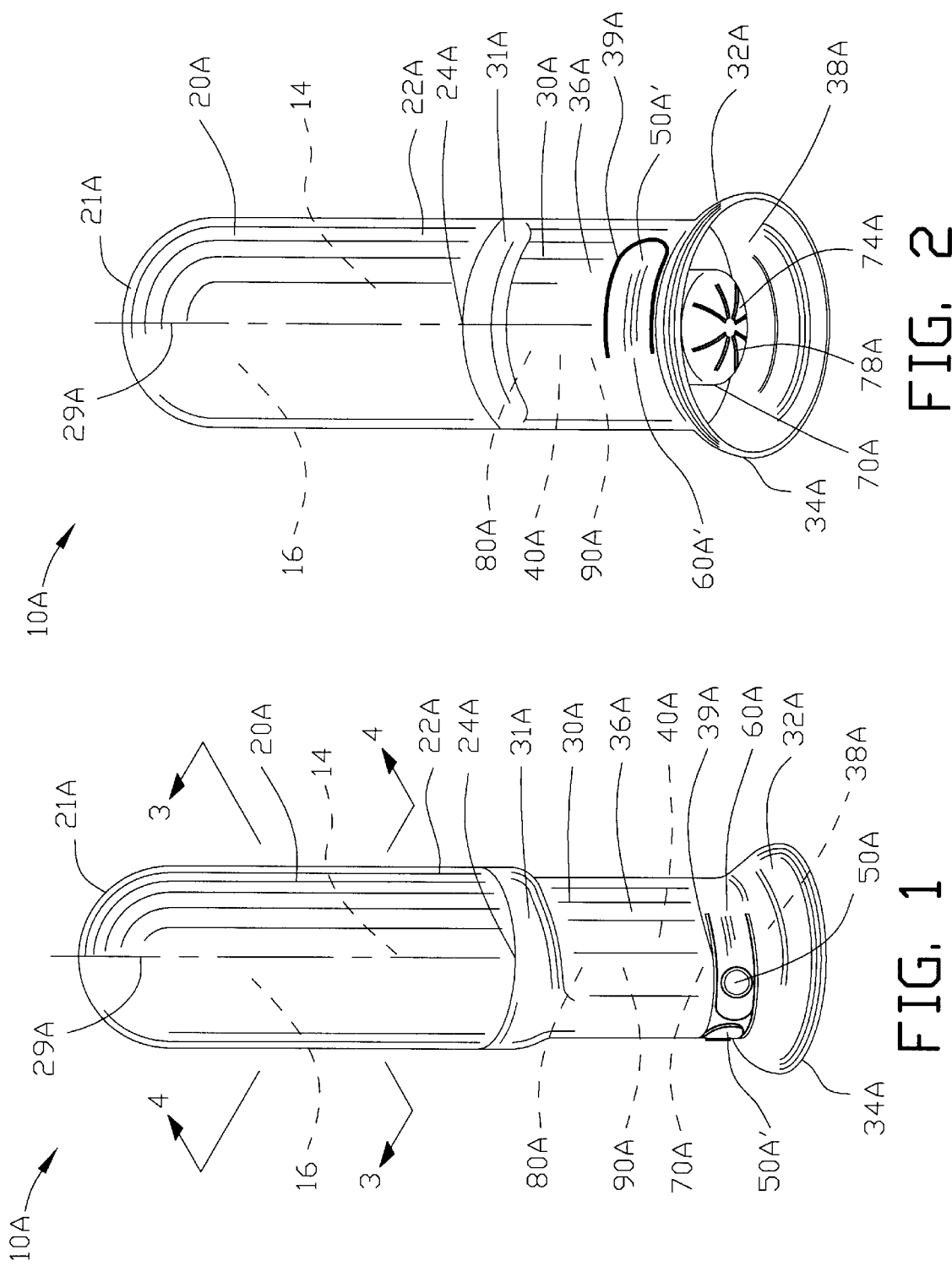

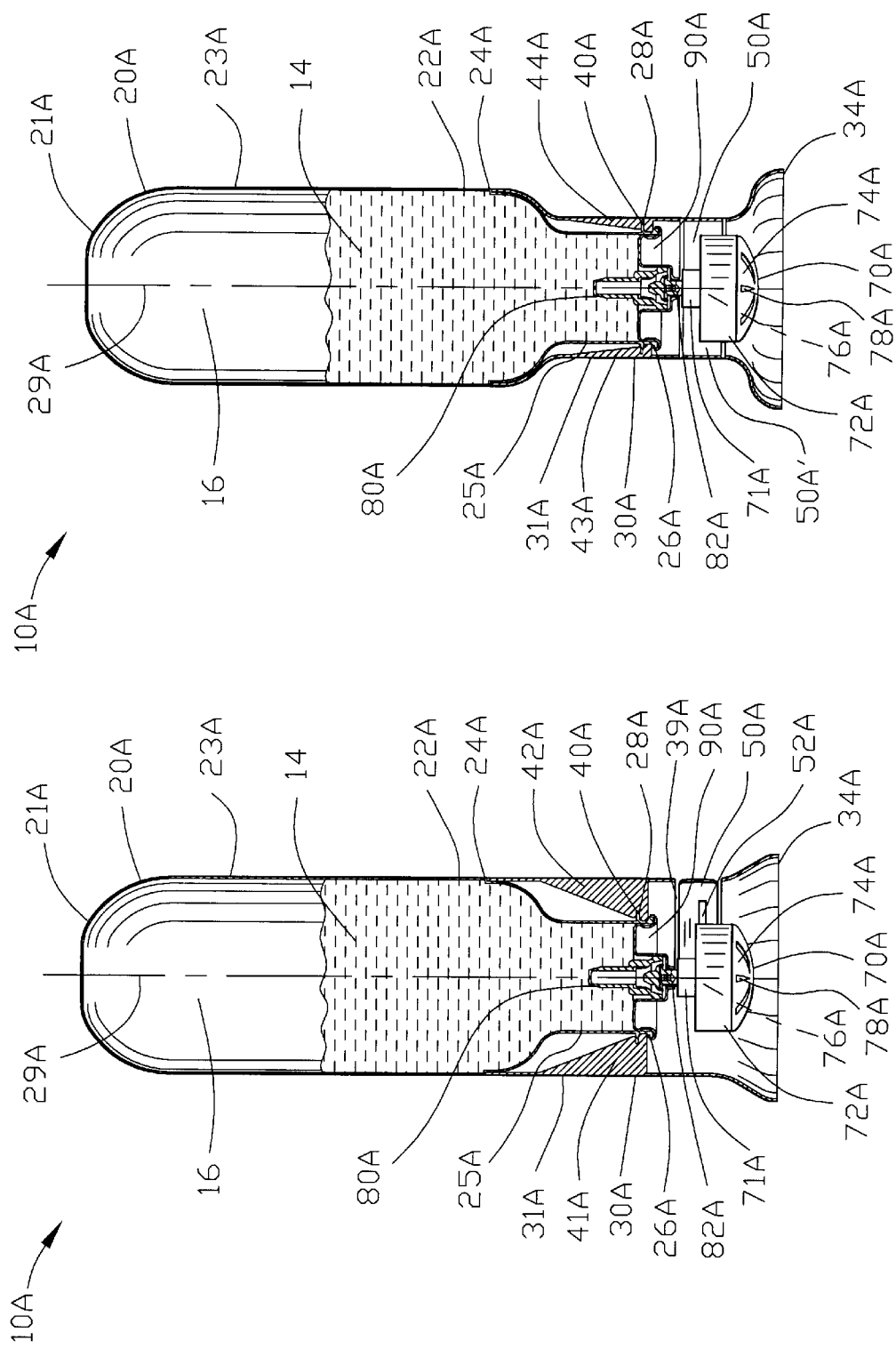

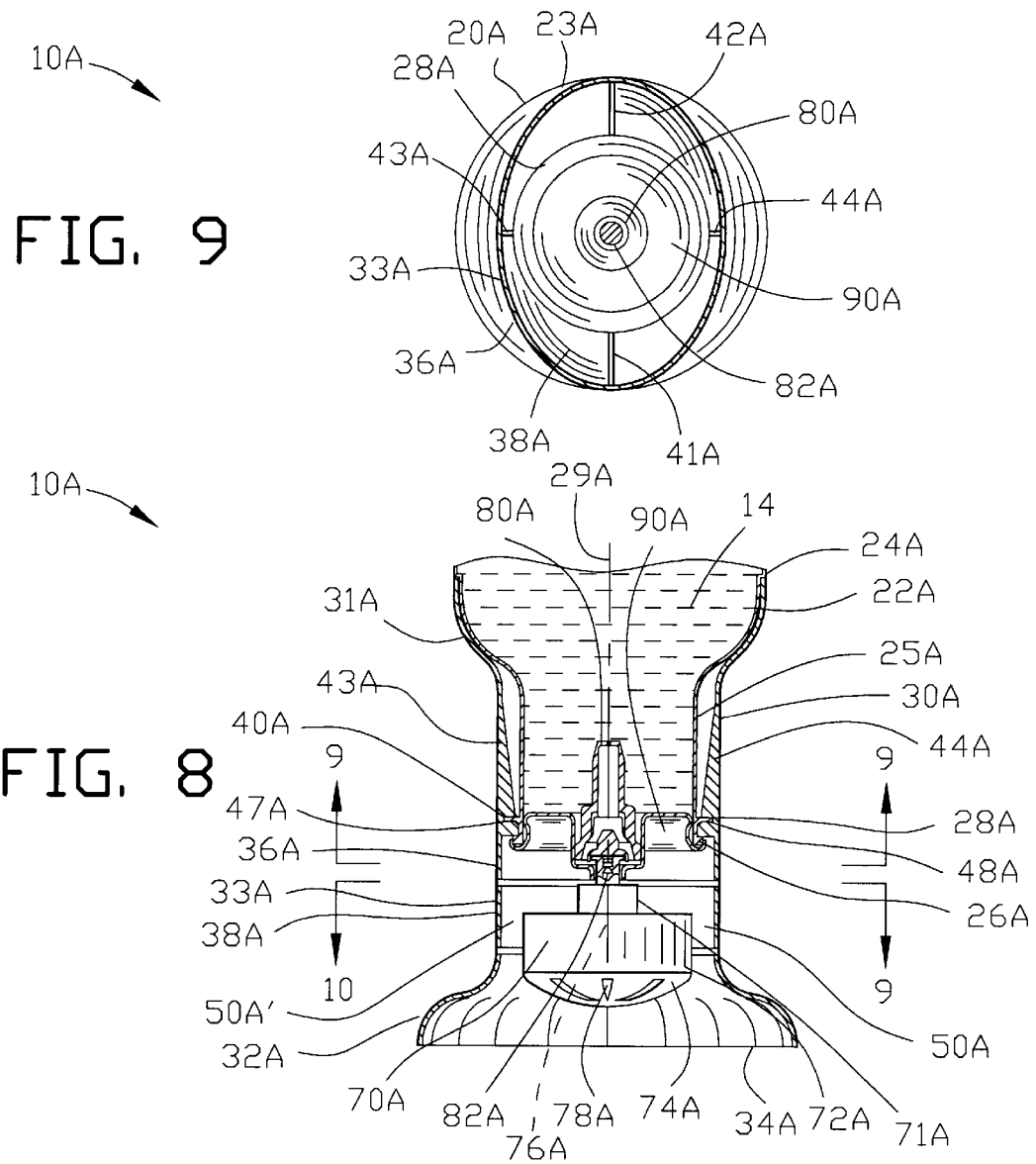
FIG. 9
FIG. 8
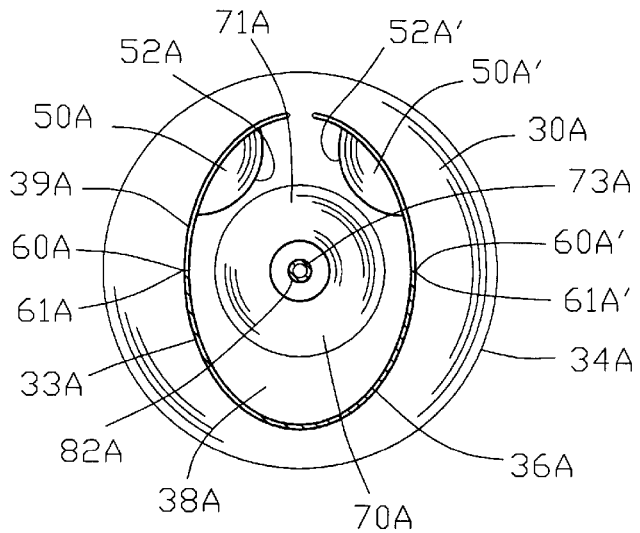
FIG. 10

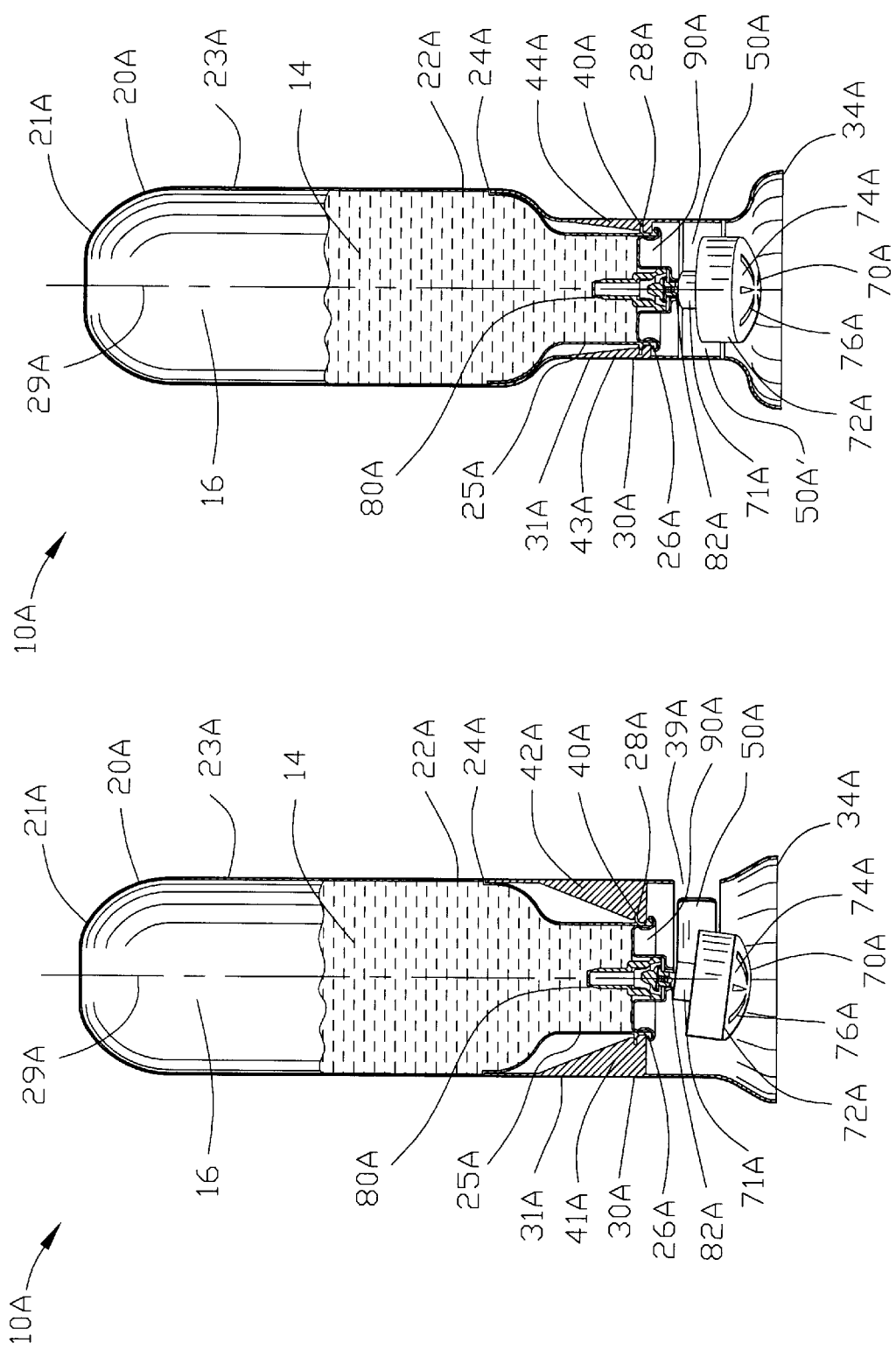

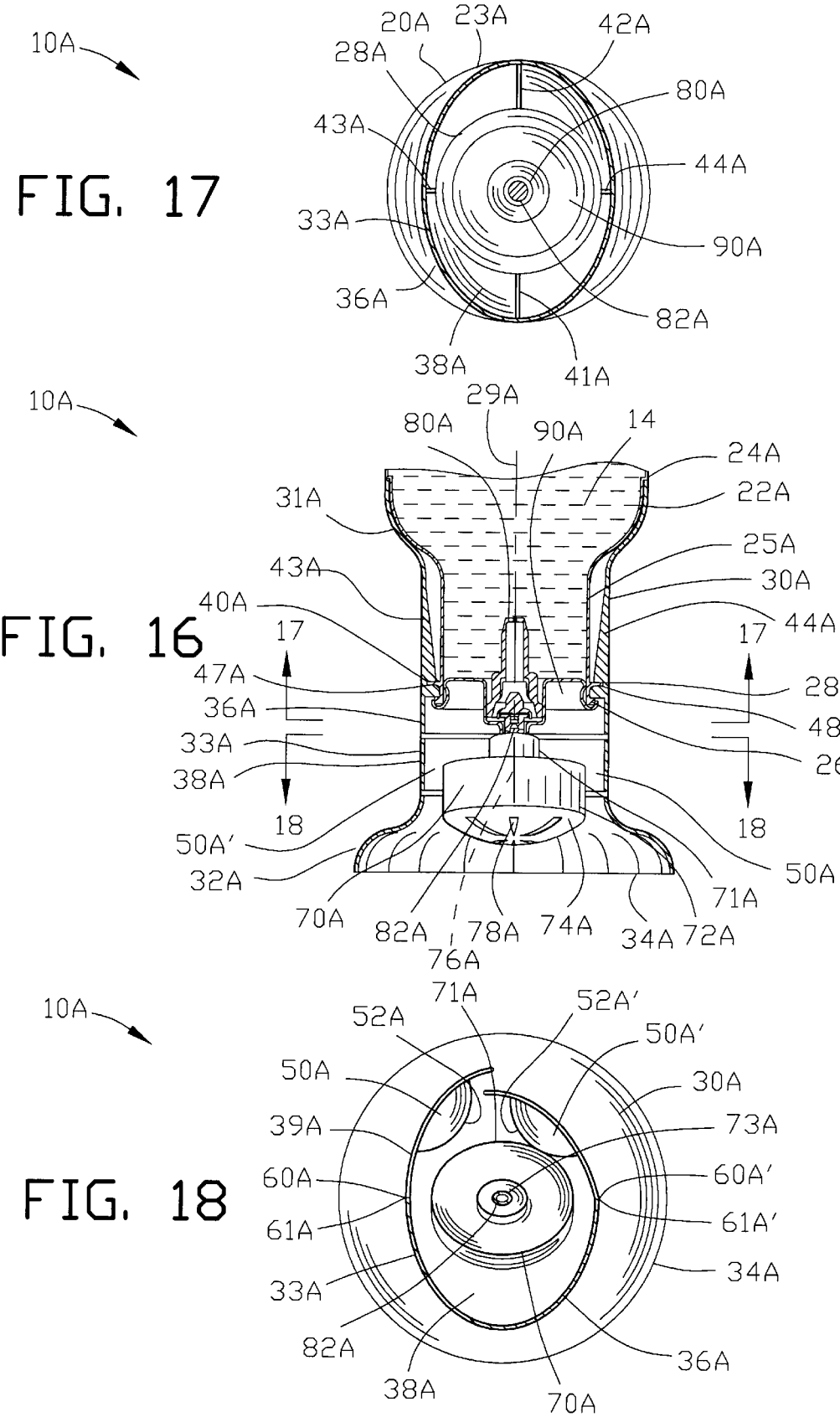

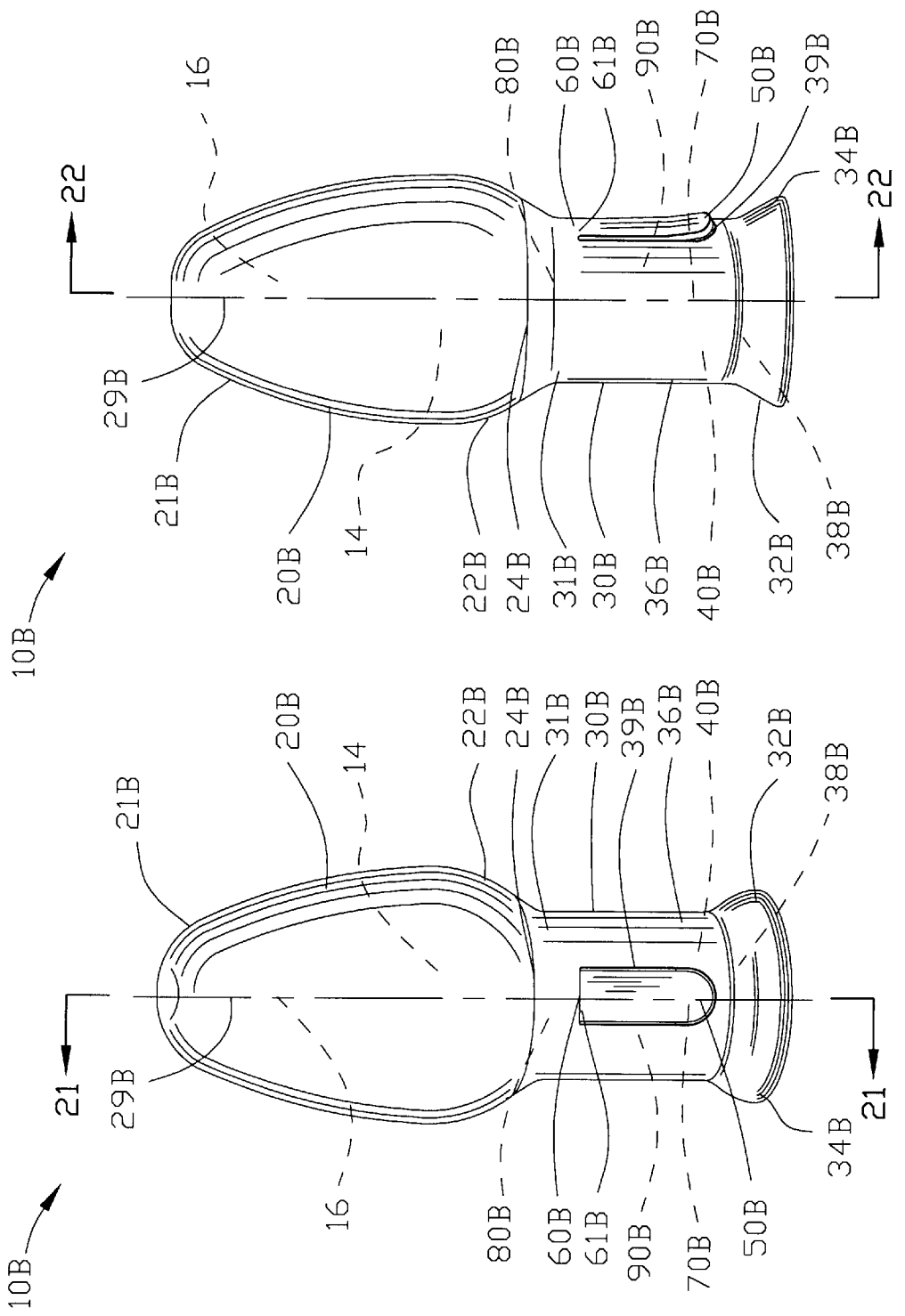

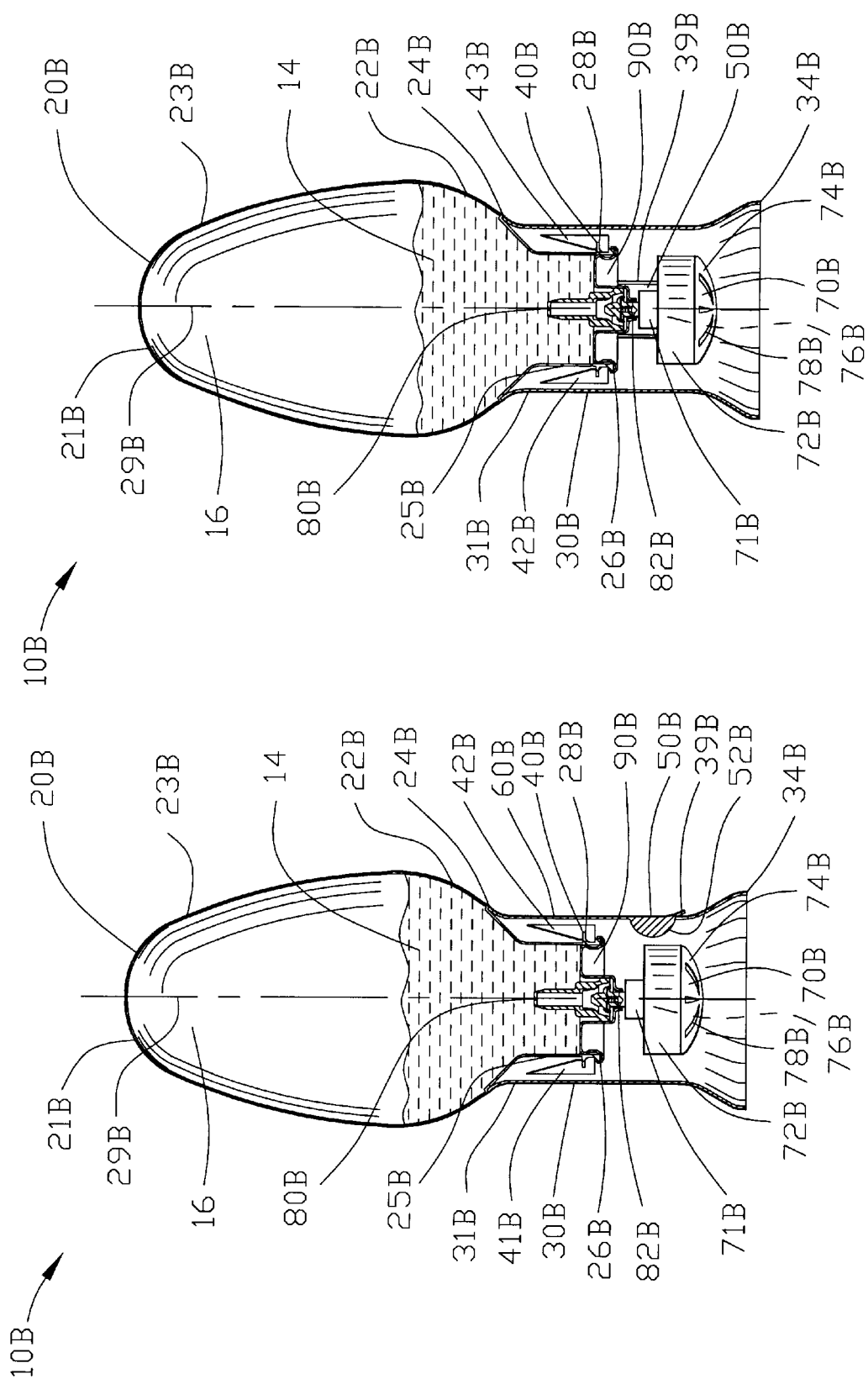

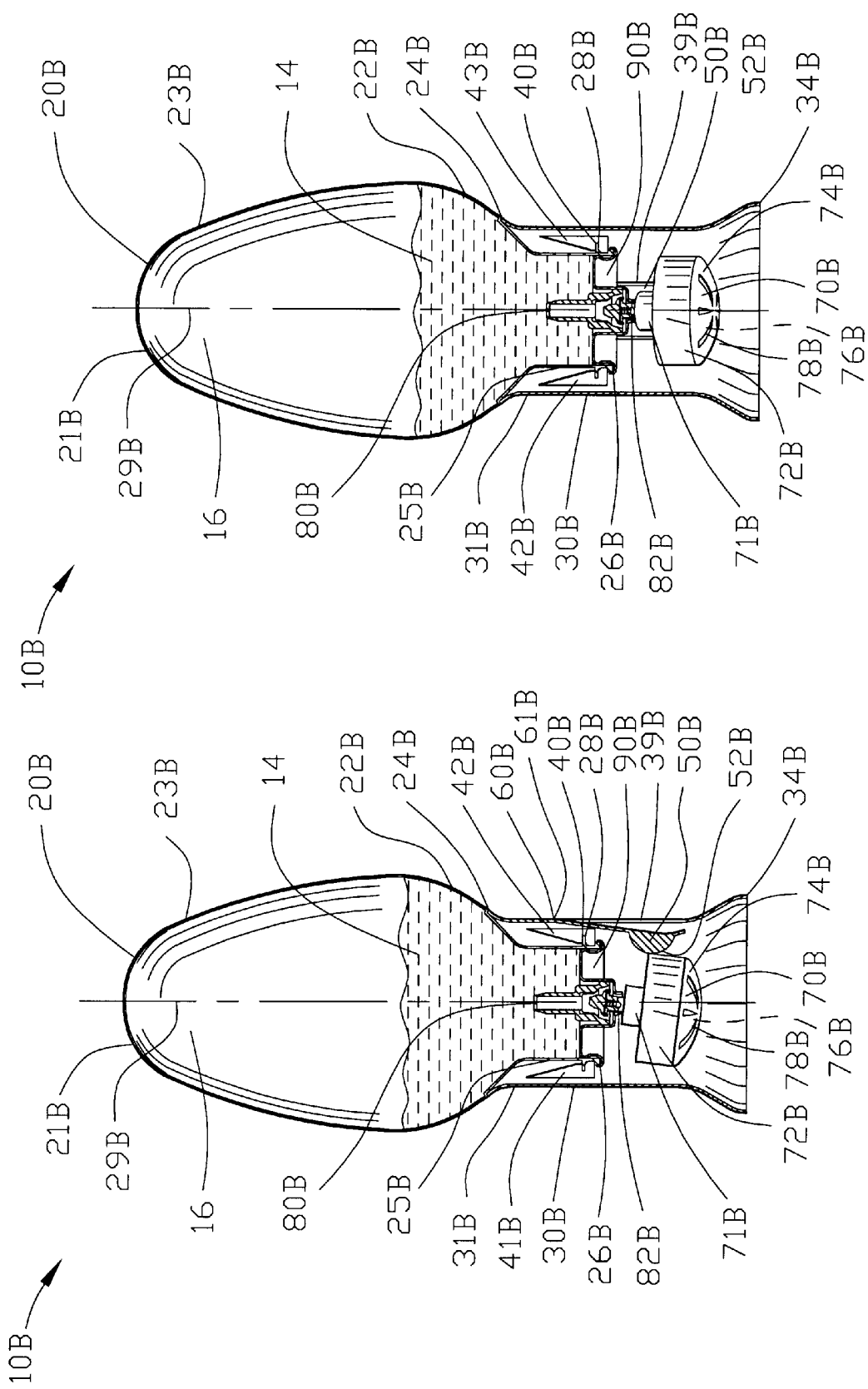

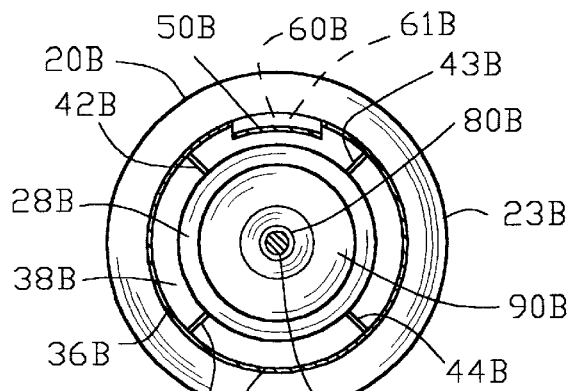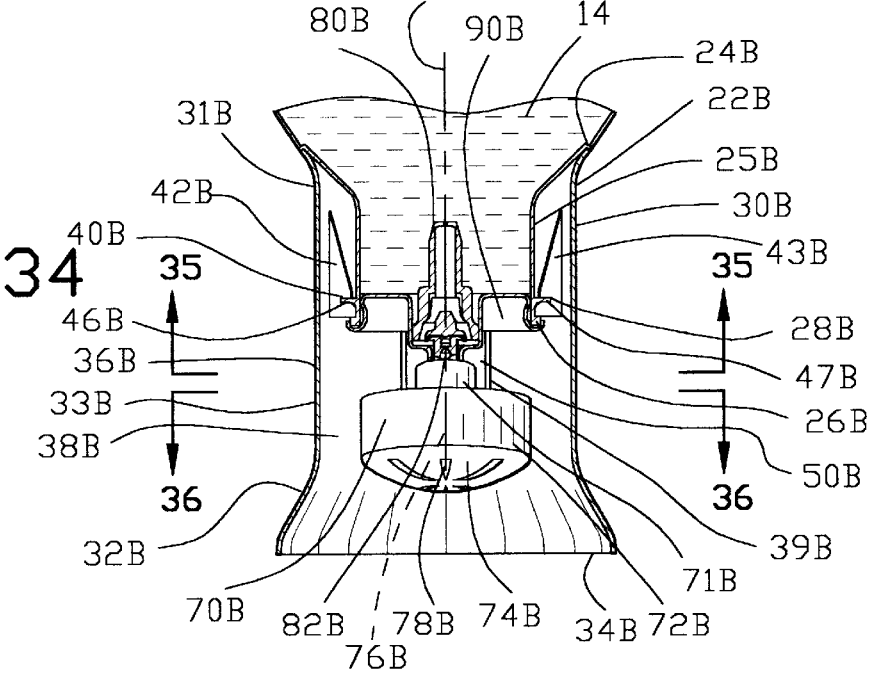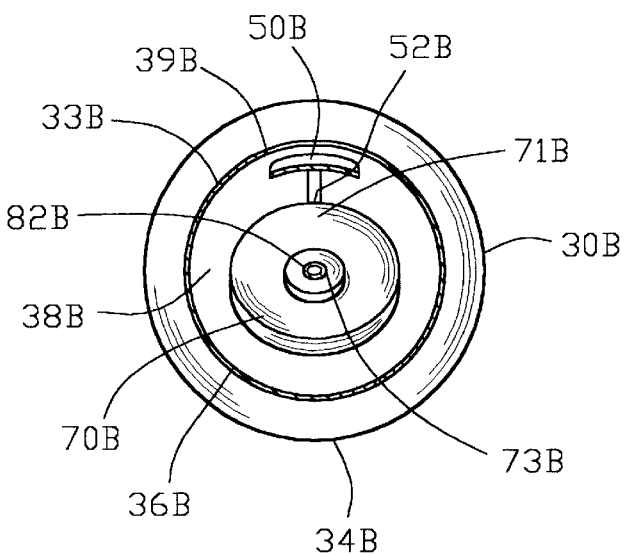

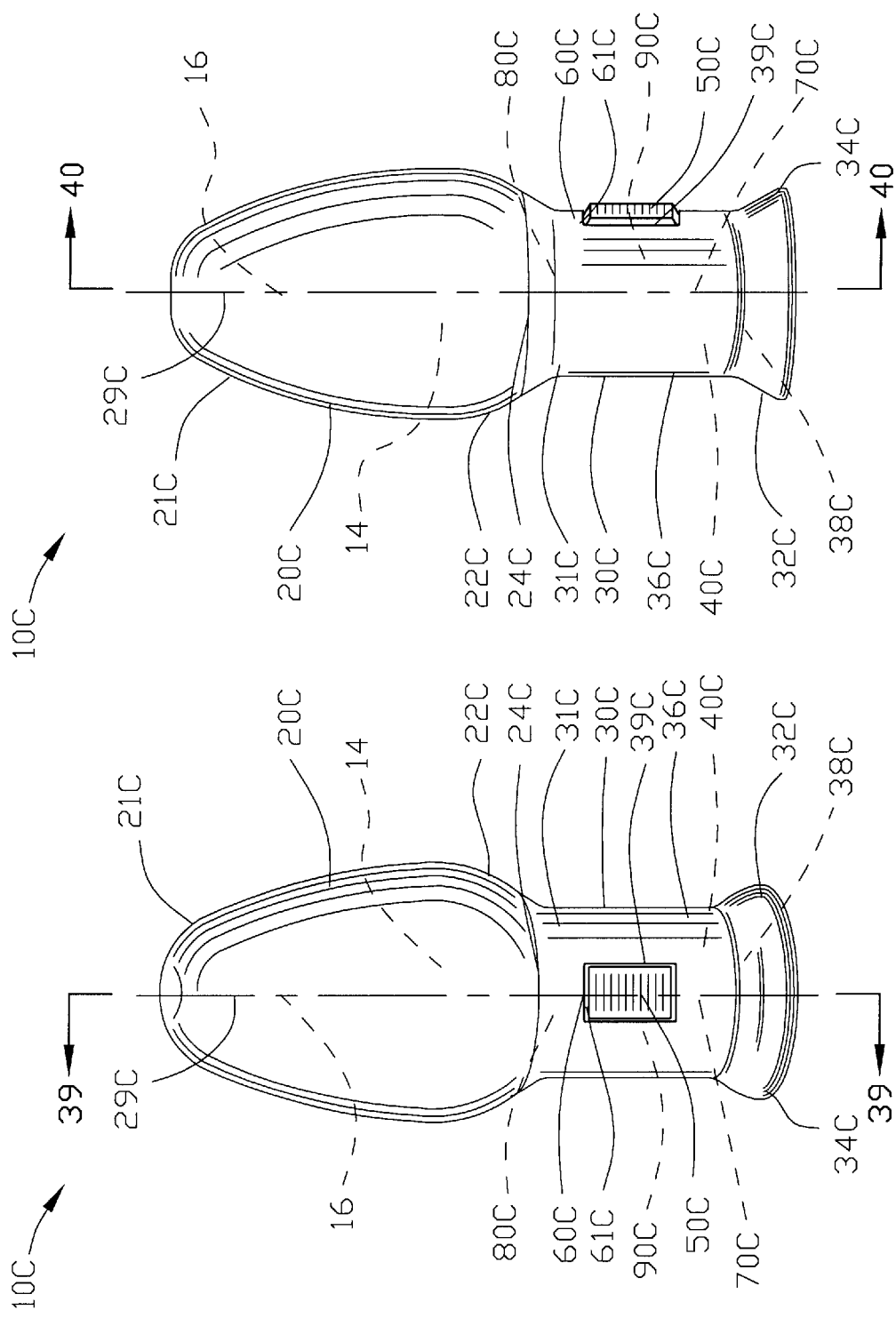

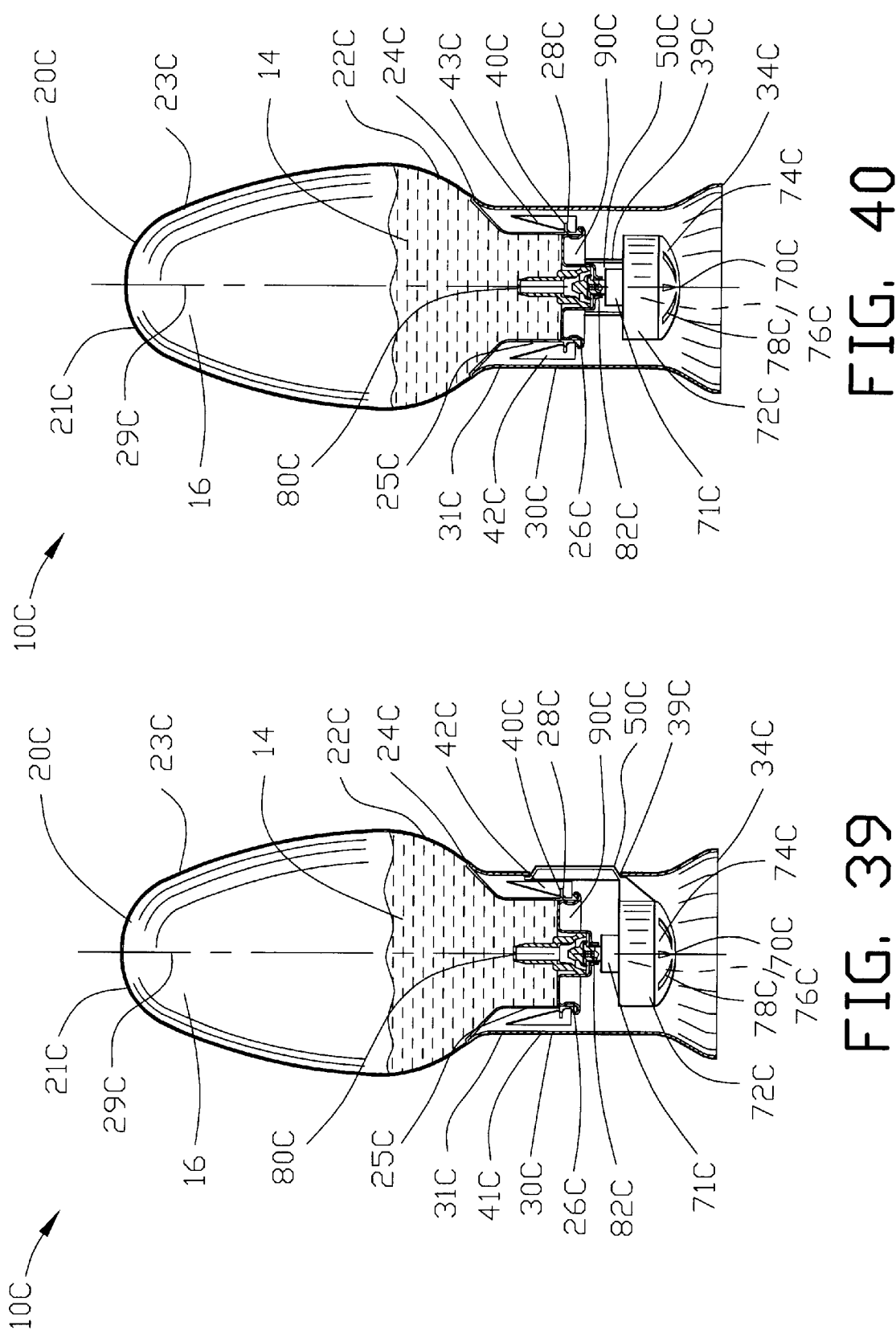

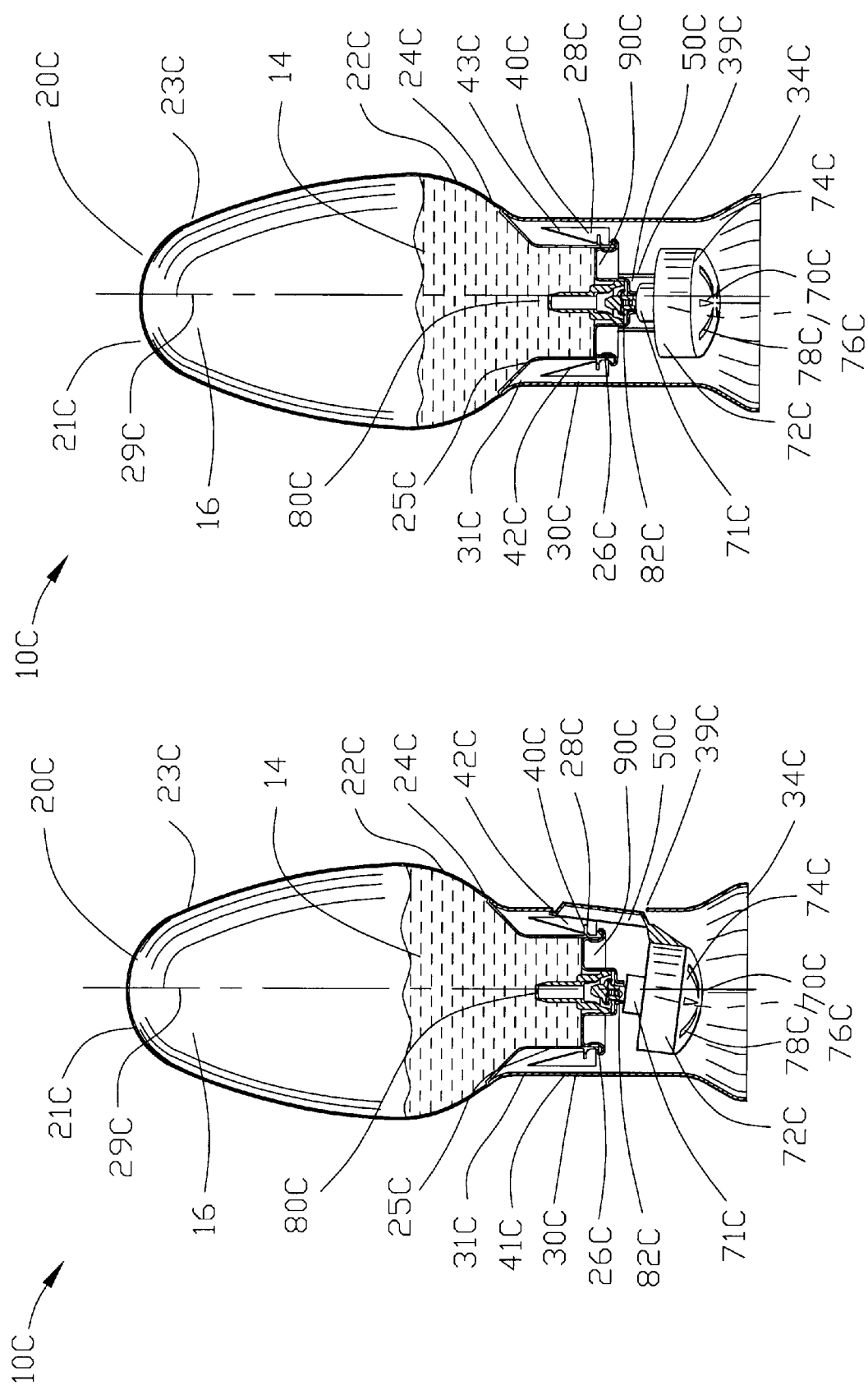

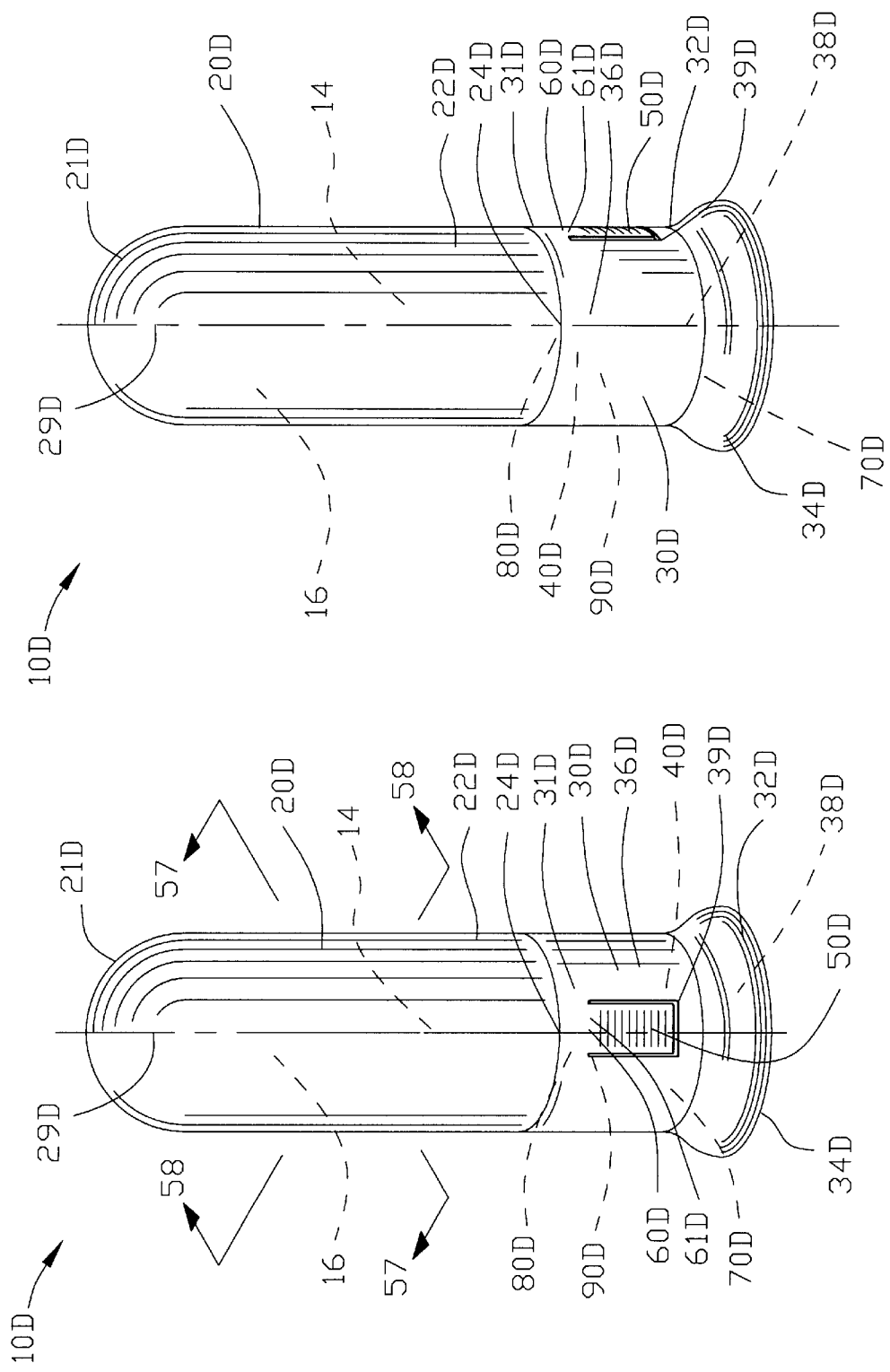

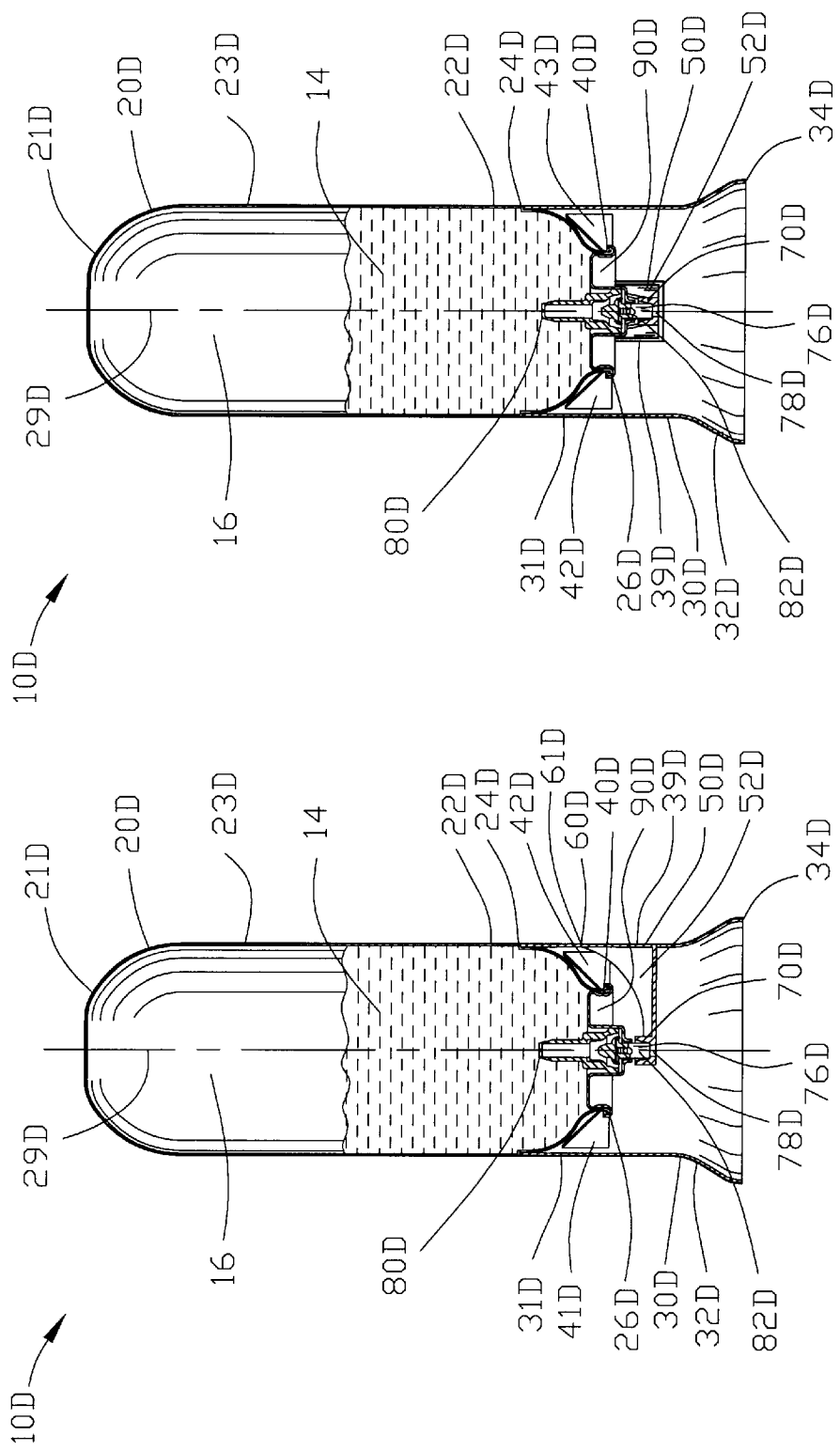

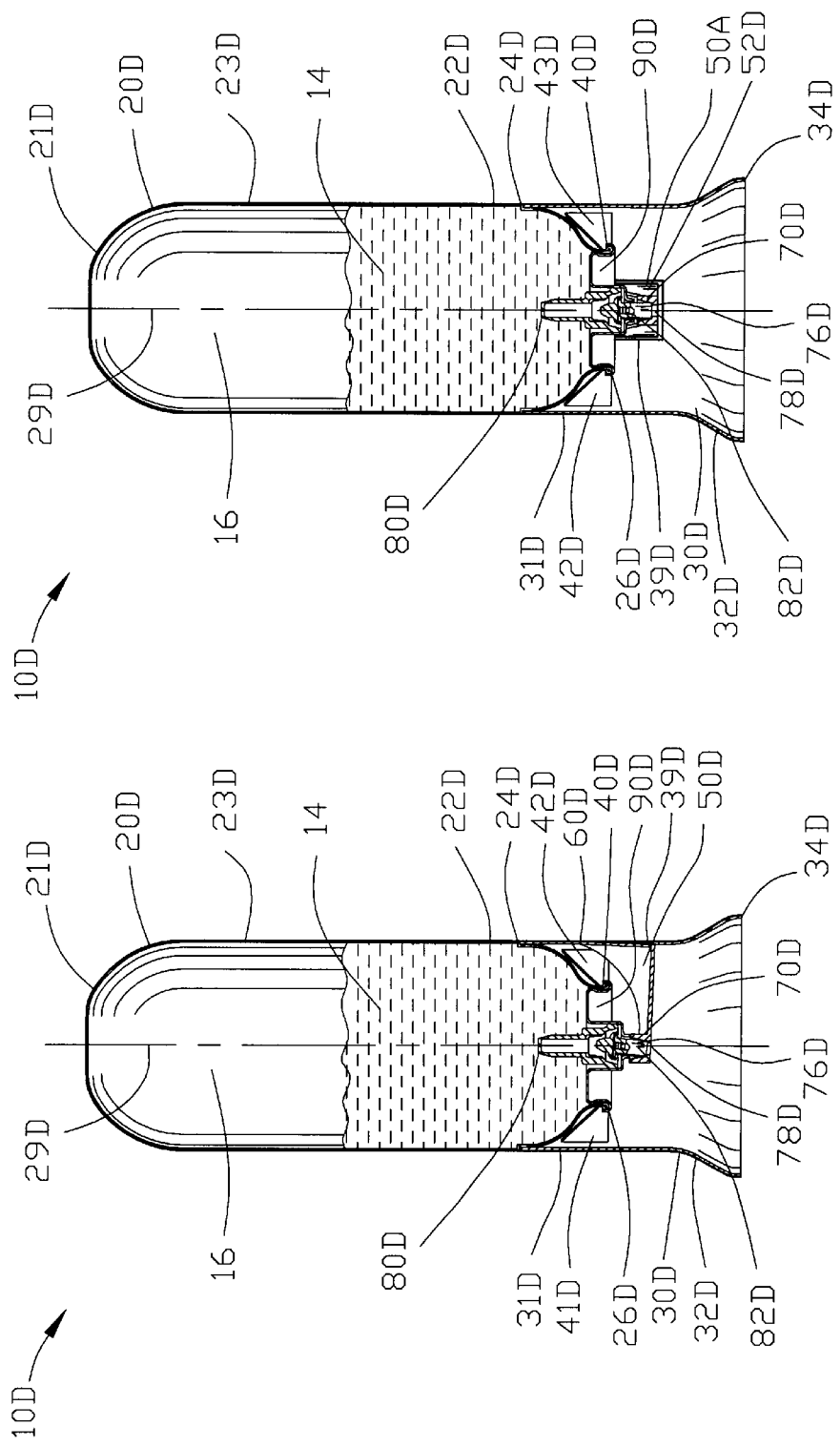

INVERTED AEROSOL DISPENSER

CROSS-REFERENCE TO RELATED APPLICATIONS

This application claims benefit of U.S. Patent Provisional application Ser. No. 60/179,792 filed Feb. 2, 2000. All subject matter set forth in provisional application Ser. No. 60/179,792 is hereby incorporated by reference into the present application as if fully set forth herein.

BACKGROUND OF THE INVENTION

1. Field of the Invention

This invention relates to aerosol dispensing devices and more particularly to an improved aerosol dispensing device for discharging an aerosol product in a generally downwardly direction.

2. Description of the Prior Art

An aerosol dispensing device comprises an aerosol valve located internal an aerosol container. The aerosol valve is biased into a closed position. A valve stem cooperates with the aerosol valve for opening the aerosol valve. An actuator engages with the valve stem to open the aerosol valve for dispensing an aerosol product from the aerosol container. The aerosol product is dispensed from the aerosol valve through a spray nozzle.

Various types of actuators have been utilized by the prior art for actuating an aerosol dispensing device. The first and the most basic type of actuator for an aerosol dispensing device is an actuator button that is affixed to the valve stem. A depression of the actuator button depresses the valve stem to open the aerosol valve for dispensing the aerosol product from the aerosol container. A protective cap is utilized for engaging with a rim of the aerosol container for inhibiting accidental actuating of the aerosol button.

The second type of actuator for an aerosol dispensing device is an aerosol overcap. The aerosol overcap replaces the conventional protective cap and includes an actuator for actuating the aerosol valve of the aerosol dispensing device. The aerosol overcap comprises a base engagable with the rim of the aerosol container for mounting the overcap to the aerosol container. The aerosol over cap includes an actuator pivotably mounted to the overcap base and engaging with the valve stem. The movement of the actuator of the aerosol overcap causes a depression of the valve stem to open the aerosol valve for dispensing the aerosol product from the aerosol container.

A third type of actuator for actuating an aerosol dispensing device is a trigger device. In this third type of actuators, a base is mounted either to the container rim or the mounting cup rim for supporting a trigger. The trigger is engagable with the valve stem. A movement of the trigger from an extended position to a protracted position depresses the valve stem to open the aerosol valve for dispensing the aerosol product from the aerosol container. The following United States Patents represent some of the trigger devices for dispensing the aerosol product from the aerosol container.

Aerosol dispenser devices traditionally dispense lower viscosity aerosol products such as hair spray, paint, deodorant, and the like in a spray form. The spray nozzle and aerosol valve is traditionally located on the top of the aerosol container for dispensing the aerosol products through the spray nozzle in an upright position.

Typically, high viscosity aerosol products like shaving gels as well as foaming aerosol products such as shave cream are stored in an upright position and are dispensed in an upright to horizontal position. Other high viscosity foaming aerosol products such as hair mousse and rug cleaner are stored in an upright position but are dispensed in an inverted position.

The high viscosity foaming aerosol products that are dispensed in an inverted position are not designed to dispense in an upright position. If these foaming aerosol products are actuated in a upright oriented position, only the aerosol propellant would escape from the aerosol container and the aerosol product would remain in the aerosol container. This loss of the aerosol propellant may deplete the aerosol propellant prior to the complete dispensing of the aerosol product from the aerosol container.

U.S. Pat. No. 1,265,177 to Coleman discloses a receptacle including a cylindrical body having an outwardly flaring supporting flange fixed to its lower end. A bottom wall is secured in the cylindrical body above the point of connection of the flange. The flange is provided with an observation opening in one side thereof. A valve casing is connected to the bottom wall and depending therefrom. A rotary valve member is mounted in the casing to control the discharge of the contents of the receptacle. The valve has a stem rotatably supported in the flange.

U.S. Pat. No. 2,765,959 to Elliott discloses a dispensing receptacle for cans of pressurized material of the type having a tiltable valve controlling spout. The can containing receptacle has an open bottom and an open top and a closure for the top. Means hold a can in the container with the dispensing spout extending through the open bottom. The means includes shoulders in the receptacle and a spring between the closure and the bottom of the can biasing the can against the shoulders. The can is telescoped within the receptacle. Laterally movable means extends through the side wall of the receptacle for engaging and tilting the tiltable valve controlling spout. The last mentioned means comprises a stem removably abutting the spout. Spring means biases the stem outwardly of the receptacle. A push bottom on the outer end of the stem moves the stem inwardly to tilt the spout.

U.S. Pat. No. 3,272,392 discloses a dispensing package for materials under pressure comprising a container having a material under pressure therein. Valve means is mounted on the container for dispensing said material on the operation thereof. The valve means includes a projecting stem portion movable relative to said container for operating said valve means and having a passage therein for passing said material. Actuating means is operable to move said stem portion relative to said container for operating said valve means. The actuating means comprises a part connected to said stem portion. The part has means therein cooperating with the passage in said stem portion for communicating the latter outwardly of said dispensing package. The part is movable relative to said container on the application thereagainst of pressure applied from a position predeterminately located relative to said container in a direction substantially transverse to the axis of said stem portion for operating said valve means.

U.S. Pat. No. 3,759,431 to Vos discloses a pressurized package of the class that includes a container for receiving a product. Propellant means in the container discharges the product from the container. A dispensing assembly is mounted on the container characterized by an actuating lever. The actuating lever shifts to displace a flexible resilient valve body member from a position in which its discharge orifice-containing surface is in scaled engagement at least partially effected by the internal container pressure with a valve cap to a position in which it is aligned with an exit opening of the overcap.

U.S. Pat. No. 3,979,163 discloses a cleaning and scrubbing tool having a cleaning head and aerosol can handle in which a suitably operational scrub pad is supported by head bracket extension in free cleaning liquid passing relation, interlocked with portions of the pad by localized deflection of the extension, suitably by locally heating or solvating the extension to deflectable condition within the pad interior.

U.S. Pat. No. 4,416,398 discloses a plural spray rate aerosol assembly for use with an aerosol container having a plural spray rate valve. The assembly comprises an actuator button having a terminal orifice connected through a valve stem to the plural spray rate valve for enabling a first discharge rate of the aerosol product from the terminal orifice upon opening the valve in a first position and for enabling a second discharge rate of the aerosol product from the terminal orifice upon opening the valve in a second position. An overcap is rotatably secured to the aerosol container and includes a finger actuator movably mounted relative to the overcap. A non-symmetrical aperture is disposed in either the actuator button or the finger actuator for cooperation with a non-symmetrical element in the other of the actuator button and the finger actuator. The non-symmetrical element is inhibited from entering the non-symmetrical aperture for transferring the finger movement of the operator to open the valve in the first position upon a first selected orientation of the finger actuator relative to the actuator button. The non-symmetrical element enters the non-symmetrical aperture for transferring the finger movement of the operator to open the valve in the second position upon a second selected orientation of the finger actuator relative to the actuator button.

U.S. Pat. No. 5,385,272 to Aoun discloses a hand held, free standing, bottom dispensing dispenser, generally made of plastic, for the dispensing of thick liquids such as lotions, shampoos and processed foodstuff, having a resiliently walled reservoir that sits atop a stand that offers fulcrum for a mechanical linkage. The linkage has a top portion engaged to the reservoir side wall allowing the user's hand to grasp and manipulate the linkage while grasping and manipulating the reservoir. A bottom portion is coupled to dispensing valve disposed and adapted to open and close a discharge element affixed to an outlet in the bottom end of the reservoir. Thus, when hand pressure is applied to the linkage top portion at the same time the reservoir is squeezed and the motion transmitted by the linkage to the dispensing valve opens the latter to dispense a portion of the content. When pressure is relieved, the resilient reservoir side wall rebounds back to its initial shape and, the reservoir side wall being engaged to the linkage moves the latter back to its initial position. Thus while causing the dispensing valve to gradually close, the reservoir side wall outward movement induces in the reservoir an air flow that draws the fluid in the discharge element in therewith. The dispenser content is always located in the lower part of the reservoir near its aperture, ready to be dispensed therefore making possible the dispensing of virtually all the content.

U.S. Pat. No. 5,957,336 to Radassao et al. discloses a viscous fluid dispenser is provided including an upper extent constructed from a flexible material and having a top face and a peripheral side wall with an inverted frustoconical configuration defining a lower peripheral edge. Further provided is a lower extent constructed from a rigid material and having a planar bottom face coupled with respect to the lower peripheral edge of the upper extent. The bottom face of the lower extent has at least one bore formed therein. Next provided is a lid hingably coupled to the lower extent for selectively closing the bore.

U.S. Pat. No. 6,010,042 to Boucher et al. discloses a base end dispensing container, especially suitable for dispensing viscous flowable liquid consumable products is disclosed. The container includes an elongated, squeezable, container having an inner chamber for holding the viscous flowable liquid consumable products. A base dispensing valve, a top end valve operating mechanism and an attached support structure support the container in an upright position a distance front a surface upon which the container is placed. The base end dispensing valve includes a sloping container floor terminating at a substantially flat section, upon which a rotationally operable valve gate rests. The substantially flat floor section of the container includes at least one dispensing opening intermediate the interior chamber of the container and the outside of the container. The valve gate is selectively operated between an open and shut position by the top end valve operating mechanism via a valve driven shaft which connects the valve operating mechanism with the rotationally operable valve gate.

U.S. Pat. No. D293,213 discloses a design patent for an aerosol overcap physically located on an top portion of the aerosol container for discharging an aerosol product in a conventional upright manner.

One recently designed aerosol dispenser is stored in an inverted position whereat the overcap, spray nozzle and the aerosol valve are located on the bottom of the aerosol container. Although this aerosol dispenser is stored in an inverted position, the aerosol container is turned upright to dispense the aerosol product from the aerosol container.

Therefore it is an object of the present invention to provide an inverted aerosol dispensing device which provides a significant advancement for the aerosol industry.

Another object of the present invention is to provide an inverted aerosol dispensing device which incorporates an undercap mounted to a bottom portion of the aerosol container for storing the inverted aerosol dispensing device in an inverted position.

Another object of the present invention is to provide an inverted aerosol dispensing device which is capable of dispensing viscous aerosol product in downward direction.

Another object of the present invention is to provide an inverted aerosol dispensing device that incorporates a wide base of undercap to provide a more stable base for storage relative to a conventional overcap mounted to a top portion of the aerosol container.

Another object of the present invention is to provide an inverted aerosol dispensing device which incorporates a one-piece undercap and actuator assembly.

Another object of the present invention is to provide an inverted aerosol dispensing device wherein the actuator may be molded in a single molding process with an undercap with an integral hinge for pivotable mounting the actuator relative to the aerosol container.

Another object of the present invention is to provide an inverted aerosol dispensing device which incorporates an actuator having a lower actuation force relative to a conventional aerosol dispensing device.

Another object of the present invention is to provide an inverted aerosol dispensing device which is easier to dispense an aerosol product into the hand of a user relative to a conventional aerosol dispensing device.

Another object of the present invention is to provide an inverted aerosol dispensing device which is suitable for use with plastic containers.

Another object of the present invention is to provide an inverted aerosol dispensing device incorporating an ergonomically designed container and undercap suitable for use by an operator with wet hands.

Another object of the present invention is to provide an inverted aerosol dispensing device that is actuated with a squeezing motion.

Another object of the present invention is to provide an inverted aerosol dispensing device which is economical to manufacture and is economical to install on the aerosol dispensing device.

The foregoing has outlined some of the more pertinent objects of the present invention. These objects should be construed as being merely illustrative of some of the more prominent features and applications of the invention. Many other beneficial results can be obtained by applying the disclosed invention in a different manner or modifying the invention with in the scope of the invention. Accordingly other objects in a full understanding of the invention may be had by referring to the summary of the invention and the detailed description describing the preferred embodiment of the invention.

SUMMARY OF THE INVENTION

A specific embodiment of the present invention is shown in the attached drawings. For the purpose of summarizing the invention, the invention relates to an inverted aerosol dispensing device comprising an aerosol container extending between a top portion and a bottom portion for containing an aerosol product and an aerosol propellant therein. An aerosol valve is located at the bottom portion of the aerosol container. The aerosol valve has a valve stem for displacing the aerosol valve from a biased closed position to an open position to discharge the aerosol product from the valve stem. An undercap is secured to the bottom portion of the aerosol container for supporting the aerosol container on a supporting surface. An actuator is movably mounted relative to the undercap for moving the valve stem upon displacement of the actuator for discharging the aerosol product from the valve stem in a generally downward direction through the undercap.

In a more specific example of the invention, the top portion of the aerosol container is a closed top portion. The aerosol container defines a container rim for supporting an aerosol mounting cup to secure the aerosol valve to the aerosol container. The aerosol valve is located at the bottom portion of the aerosol container with the aerosol valve being located internal the aerosol container with the valve stem extending from the aerosol container.

In one example of the invention, the aerosol valve is a tilt valve wherein a tilting of the valve stem displaces the aerosol valve from the biased closed position to the open position. In another example of the invention, the aerosol valve is a vertical action valve wherein a vertical movement of the valve stem displaces the aerosol valve from the biased closed position to the open position.

In still another example of the invention, the actuator is pivotably mounted to the aerosol container for moving the valve stem upon pivoting of the actuator. The undercap is secured to the bottom portion of the aerosol container with the actuator being pivotably mounted to the undercap for moving the valve stem upon pivoting of the actuator. The actuator may be integrally connected to the undercap through an hinge integrally molded as a one-piece plastic unit with the undercap. In a further example of the invention, the actuator is slidably mounted relative to the aerosol container for moving the valve stem upon sliding of the actuator.

In still another example of the invention, the inverted aerosol dispensing device includes a valve button having a terminal orifice secured to the valve stem. The actuator moves the valve button upon displacement of the actuator for moving the valve stem to direct the aerosol product through the valve stem to be discharged from the terminal orifice of the valve button in a generally downward direction. An aperture may be defined in the undercap. The valve stem direct the aerosol product in a generally downward direction through the aperture defined in the undercap.

The foregoing has outlined rather broadly the more pertinent and important features of the present invention in order that the detailed description that follows may be better understood so that the present contribution to the art can be more fully appreciated. Additional features of the invention will be described hereinafter which form the subject matter of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention.

BRIEF DESCRIPTION OF THE DRAWINGS

For a fuller understanding of the nature and objects of the invention, reference should be made to the following detailed description taken in connection with the accompanying drawings in which:

FIG. 1 is a top isometric view of a first embodiment of an aerosol dispensing device incorporating the present invention;

FIG. 2 is a bottom isometric view of the aerosol dispensing device of FIG. 1;

FIG. 3 is a sectional view along line 3—3 in FIG. 1 with the aerosol dispensing device being shown in an unattended condition;

FIG. 4 is a sectional view along line 4—4 in FIG. 1 with the aerosol dispensing device being shown in an unattended condition;

FIG. 8 is an enlarged view of a portion of FIG. 4;

FIG. 9 is a sectional view along line 9—9 in FIG. 8;

FIG. 10 is a sectional view along line 10—10 in FIG. 8;

FIG. 11 is a sectional view similar to FIG. 3 with the aerosol dispensing device being shown in a dispensing condition;

FIG. 12 is a sectional view similar to FIG. 4 with the aerosol dispensing device being shown in a dispensing condition;

FIG. 16 is an enlarged view of a portion of FIG. 12;

FIG. 17 is a sectional view along line 17—17 in FIG. 16;

FIG. 18 is a sectional view along line 18—18 in FIG. 16;

FIG. 19 is a front isometric view of a second embodiment of an aerosol dispensing device incorporating the present invention;

FIG. 20 is a side isometric view of the aerosol dispensing device of FIG. 19;

FIG. 21 is a sectional view along line 21—21 in FIG. 20 with the aerosol dispensing device being shown in an unattended condition;

FIG. 22 is a sectional view along line 22—22 in FIG. 20 with the aerosol dispensing device being shown in an unattended condition;

FIG. 29 is a sectional view similar to FIG. 21 with the aerosol dispensing device being shown in a dispensing condition;

FIG. 30 is a sectional view similar to FIG. 22 with the aerosol dispensing device being shown in a dispensing condition;

FIG. 34 is an enlarged view of a portion of FIG. 30;

FIG. 35 is a sectional view along line 35—35 in FIG. 34;

FIG. 36 is a sectional view along line 36—36 in FIG. 34;

FIG. 37 is a front isometric view of a third embodiment of an aerosol dispensing device incorporating the present invention;

FIG. 38 is a side isometric view of the aerosol dispensing device of FIG. 37;

FIG. 39 is a sectional view along line 39—39 in FIG. 37 with the aerosol dispensing device being shown in an unattended condition;

FIG. 40 is a sectional view along line 40—40 in FIG. 38 with the aerosol dispensing device being shown in an unattended condition;

FIG. 47 is a sectional view similar to FIG. 39 with the aerosol dispensing device being shown in a dispensing condition;

FIG. 48 is a sectional view similar to FIG. 40 with the aerosol dispensing device being shown in a dispensing condition;

FIG. 55 is a front isometric view of a fourth embodiment of an aerosol dispensing device incorporating the present invention;

FIG. 56 is a side isometric view of the aerosol dispensing device of FIG. 55;

FIG. 57 is a sectional view along line 57—57 in FIG. 55 with the aerosol dispensing device being shown in an unattended condition;

FIG. 58 is a sectional view along line 58—58 in FIG. 56 with the aerosol dispensing device being shown in an unattended condition;

FIG. 65 is a sectional view similar to FIG. 57 with the aerosol dispensing device being shown in a dispensing condition;

FIG. 66 is a sectional view similar to FIG. 58 with the aerosol dispensing device being shown in a dispensing condition;

Similar reference characters refer to similar parts throughout the several Figures of the drawings.

DETAILED DISCUSSION

Figure 6:
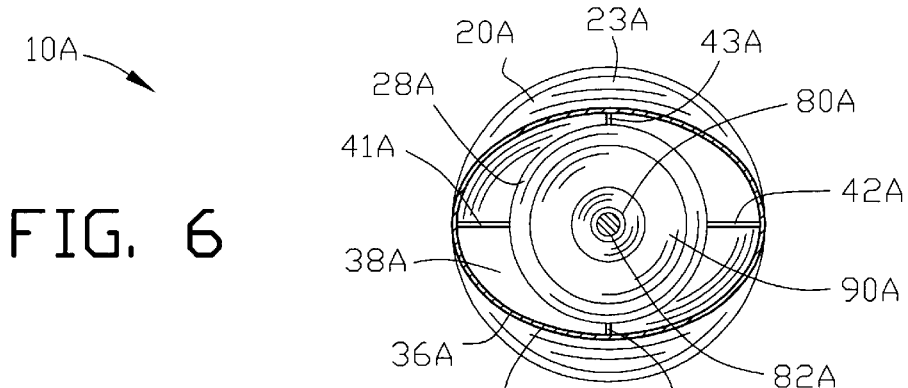
FIG. 6 is a sectional view along line 6—6 in FIG. 5.
Figure 5:
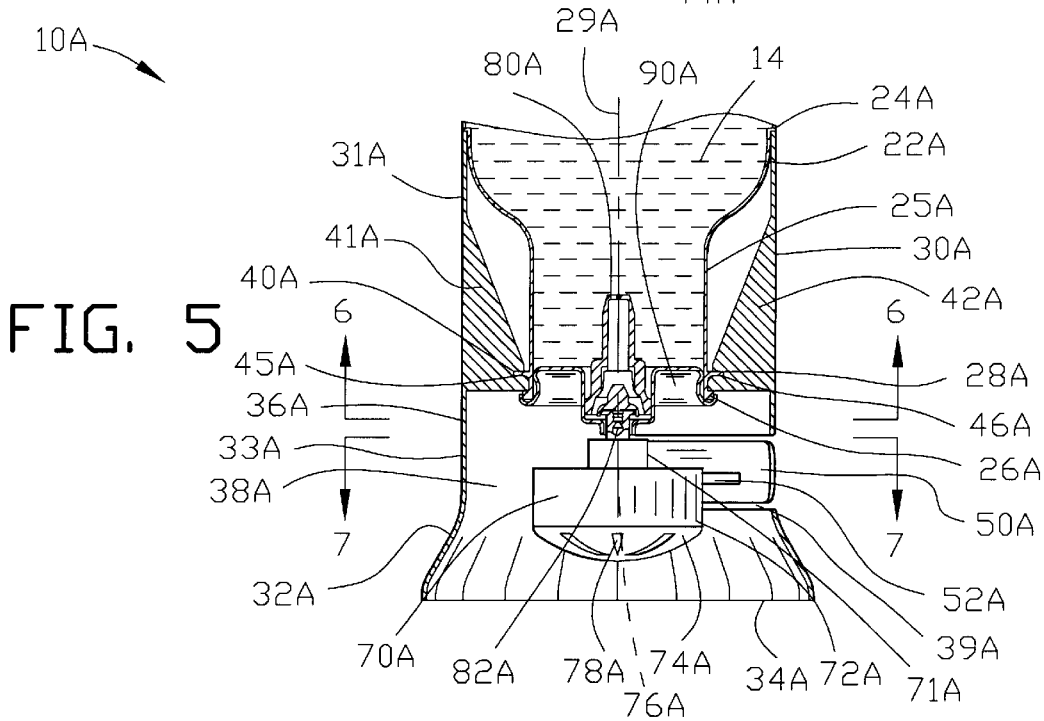
FIG. 5 is an enlarged view of a portion of FIG. 3.
Figure 7:
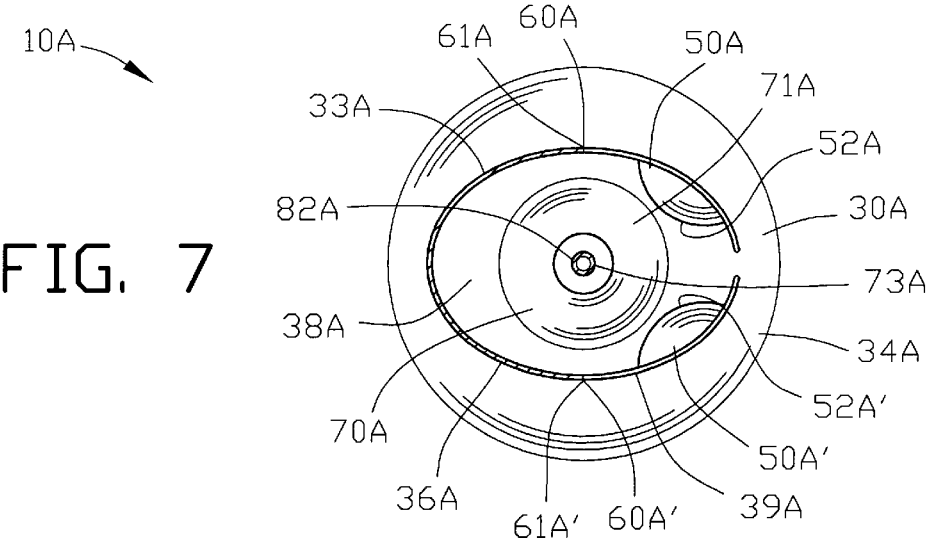
FIG. 7 is a sectional view along line 7—7 in FIG. 5.
Figure 14:
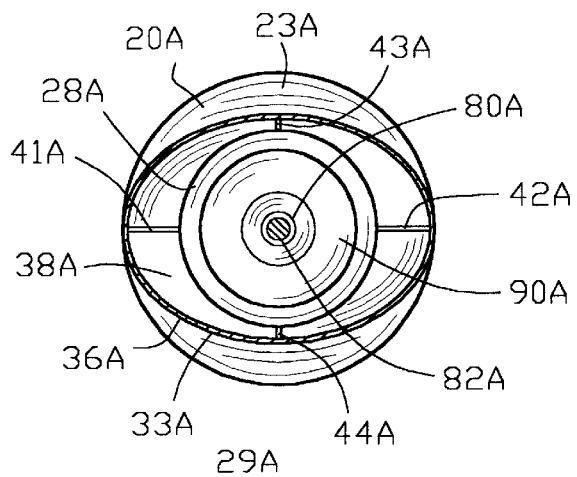
FIG. 14 is a sectional view along line 14—14 in FIG. 13.
Figure 13:
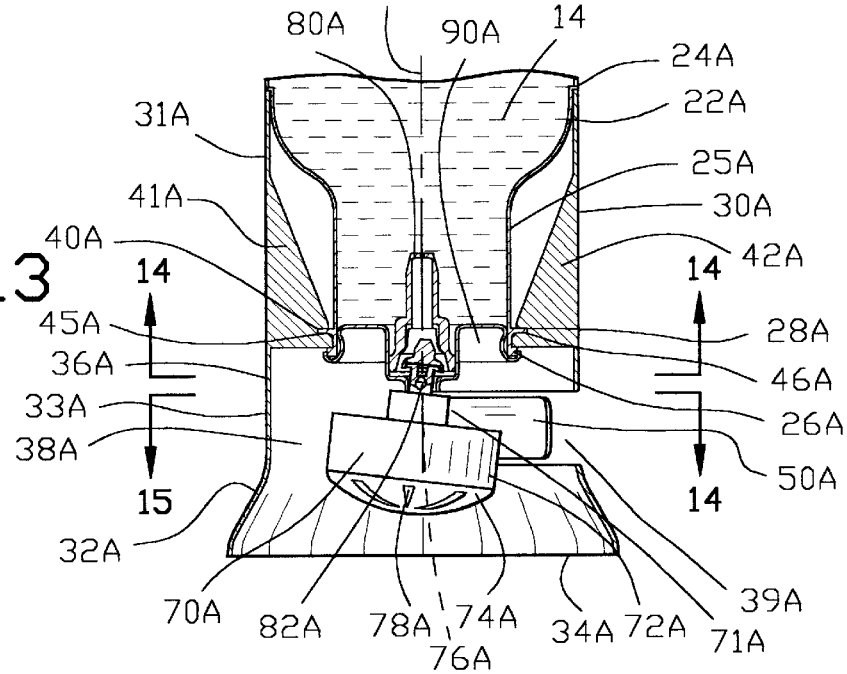
FIG. 13 is an enlarged view of a portion of FIG. 11.
Figure 15:
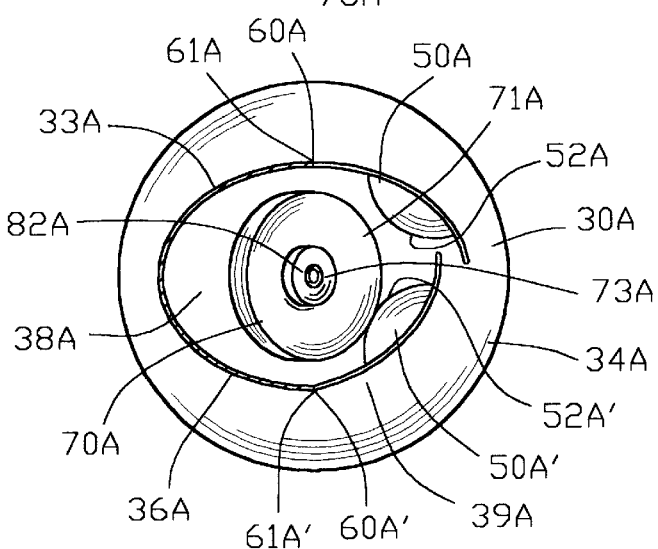
FIG. 15 is a sectional view along line 15—15 in FIG. 13.
Figure 24:
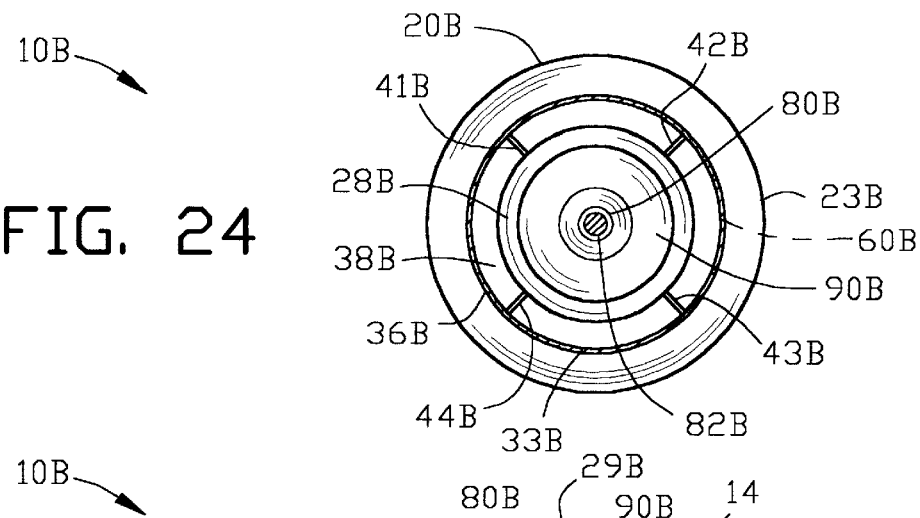
FIG. 24 is a sectional view along line 24—24 in FIG. 23.

FIGS. 1 and 2 are top and bottom isometric views of a first embodiment of an aerosol dispensing device 10A for dispensing an aerosol product 14 incorporating the present invention. The aerosol dispensing device 10A dispenses the aerosol product 14 through an aerosol propellant 16 from an aerosol container 20A.

The aerosol dispensing device 10A of the present invention enables the aerosol container 20A to be stored in an inverted position. The aerosol dispensing device 10A dispenses the aerosol product 14 under the pressure of the aerosol propellant 16 in a generally downward direction through the undercap 30A. The invention is particularly useful in dispensing viscous aerosol products 14.

FIGS. 3 and 4 are sectional views of FIG. 1 illustrating an undercap 30A secured to the aerosol container 20A by a mounting 40A for supporting the aerosol container 20A. The undercap 30A includes an actuator 50A pivotably connected to the undercap 30A by a hinge 60A. The actuator 50A is positioned for actuating a valve button 70A connected to an aerosol valve 80A mounted to the aerosol container 20A. The actuation of the aerosol valve 80A enables the aerosol product 14 to be dispensed under the pressure of the aerosol propellant 16 from the aerosol container 20A and to be discharged from the valve button 70A.

FIGS. 3 and 4 illustrate the actuator 50A in an unattended condition. The container 20A is shown as a cylindrical container of conventional design disposed in an inverted orientation. The aerosol container 20A extends between a top portion 21A and a bottom portion 22A. The top portion 21A of the aerosol container 20A is closed by an endwall. The aerosol container 20A defines a cylindrical sidewall 23A defining a container rim 24A extending about an outer diameter of the aerosol container 20A. The bottom portion 22A of the aerosol container 20A tapers radially inwardly into a neck 25A terminating in a bead 26A. A flange 28A extends radially outward about the neck 25A of the aerosol container 20A. The aerosol container 20A defines an axis of symmetry 29A.

The bead 26A supports an aerosol mounting cup 90A for sealably securing the aerosol valve 80A to the aerosol container 20A. The aerosol container 20A may be made of a metallic material or a non-metallic material. In this example, the aerosol container 20A is shown as a plastic bottle.

The aerosol product 14 is contained near the bottom portion 22A of the aerosol container 20A whereas the aerosol propellant 16 is contained near the top portion 21A of the aerosol container 20A. The aerosol dispensing device 10A is especially suited for dispensing viscous products like shampoo, hair conditioner, hair gel, hair mousse or non-foaming soap. In addition, the aerosol dispensing device 10A is especially suited for dispensing viscous food products such as ketchup, mustard, mayonnaise and the like. The aerosol dispensing device 10A is suitable also for dispensing products such as furniture polish in a downward direction through the use of a appropriate valve button 70A. The aerosol propellant 16 may be compressed gas, carbon dioxide or any other suitable propellant.

FIGS. 5–7 and 8–10 are enlarged views of portions of FIGS. 3 and 4 respectively. The undercap 30A has a top portion 31A and a bottom portion 32A with a sidewall 33A extending therebetween. The undercap 30A includes an enlarged base 34A for providing a greater stability to the aerosol dispensing device 10A. The enlarged base 34A compensates for the higher center of gravity of the aerosol dispensing device 10A than found in conventional aerosol dispensers. Preferably, the undercap 30A is formed from a unitary and resilient polymeric material such as polypropylene, polyethylene, polyolyfin or any other suitable polymeric material.

The undercap 30A includes a gripping area 36A having an elliptically-shaped cross-section. The elliptically-shaped cross-section provides a superior ergonomic shape. Preferably, the undercap 30A comprises a plastic shell defining an undercap aperture 38A. The undercap aperture 38A provides a passage for dispensing the aerosol product 14 in a generally downward direction through the undercap 30A. A sidewall orifice 39A is defined in the sidewall 33A of the undercap 30A.

The undercap 30A is secured to the aerosol container 20A by a mounting shown generally as 40A. In the example, the mounting 40A comprises a plurality of ribs 41A–44A extending inwardly from the sidewall 33A of the undercap 30A. The plurality of ribs 41A–44A having recesses 45A–48A for securing the undercap 30A to the aerosol container 20A in a snap locking engagement.

In this example of the invention, the plurality of ribs 41A–44A secures the undercap 30A to the flange 28A extending radially outward from the neck 25A of the aerosol container 20A. The recesses 45A–48A of the plurality of ribs 41A–44A received the flange 28A to secure the undercap 30A to the aerosol container 20A in a snap locking engagement. The top portion 31A of the undercap 30A is received within the container rim 24A of the aerosol container 20A.

The actuator 50A is located in the sidewall orifice 39A of the sidewall 33A of the undercap 30A for actuating the aerosol valve 80A. In this first embodiment of the aerosol dispensing device 10A, the actuator 50A is shown as plural actuators 50A and 50A' located on opposed sides of the elliptically-shaped cross-section of the gripping area 36A. The plural actuators 50A and 50A' are substantially identical to one another. Each of the plural actuators 50A and 50A' pivots about hinges 60A and 60A' having hinge axes 61A and 61A'. The hinge axes 61A and 61A' are substantially parallel to the axis of symmetry 29A extend through the aerosol container 20A. Each of the plural actuators 50A and 50A' and the hinges 60A and 60A' are integrally connected to the undercap 30A. The plural actuators 50A and 50A' pivot on hinges 60A and 60A' to extend into the sidewall orifice 39A.

The aerosol valve 80A is located at the bottom portion 22A of the aerosol container 20A. The aerosol valve 80A is secured into the aerosol mounting cup 90A in a conventional fashion. The aerosol mounting cup 90A is crimped to the bead 26A of the container 20A for sealably securing the aerosol valve 80A to the aerosol container 20A. The aerosol valve 80A is disposed within the aerosol container 20A with the valve stem 82A extending downward from the aerosol container 20A.

The valve button 70A is secured to the valve stem 82A. The valve button 70A extends between a top portion 71A and a bottom portion 72A. The top portion 71A of the valve button 70A is provided with a socket 73A for frictionally receiving the valve stem 82A of the aerosol valve 80A. The bottom portion 72A of the valve button 70A is defined by an enlarged side surface 74A. A channel 76A extends through the valve button 70A to provide fluid communication between the valve stem 82A of the aerosol valve 80A and a terminal orifice 78A of the valve button 70A.

FIGS. 11 and 12 are sectional views similar to FIGS. 3 and 4 illustrating the actuator 50A in an actuated condition. The valve stem 82A of the aerosol valve 80A displaces the aerosol valve 80A between a biased closed position as shown in FIGS. 3 and 4 to an open position as shown in FIGS. 11 and 12. When the valve stem 82A is displaced into the open position as shown in FIGS. 11 and 12, the aerosol dispensing device 10A dispenses the aerosol product 14 under the pressure of the aerosol propellant 16 in a generally downward direction through the undercap 30A from the valve button 70A.

FIGS. 13–15 and 15–18 are enlarged views of portions of FIGS. 11 and 12 respectively. The aerosol valve 80A is shown as a tilt valve wherein the tilting the valve button 70A tilts the valve stem 82A of the aerosol valve 80A. The tilting of the valve stem 82A displaces the aerosol valve 80A from the biased closed position to the open position. However, it should be understood that the invention may be modified to function with a vertical action valve wherein a vertical movement of the valve stem 82A displaces the aerosol valve 80A from the biased closed position to the open position.

The actuators 50A and 50A' are movably mounted relative to the undercap 30A for moving the valve button 70A and the valve stem 82A upon displacement of one or both of the actuators 50A and 50A'. The displacement of the actuators 50A and 50A' move the aerosol valve 80A into the open position to dispense the aerosol product 14 under the pressure of the aerosol propellant 16 in a generally downward direction through the undercap 30A.

The actuators 50A and 50A' include actuator surfaces 52A and 52A' extending radially inwardly from the actuators 50A and 50A'. The actuator surfaces 52A and 52A' engage the valve button 70A upon an inward movement of the actuators 50A and 50A'. The displacement of the actuators 50A and 50A' move the actuator surfaces 52A and 52A' into engagement with the valve button 70A to displace the aerosol valve 80A into the open position to dispense the aerosol product 14 under the pressure of the aerosol propellant 16.

In this example of the invention, the actuators 50A and 50A' are pivotably mounted relative to undercap 30A for moving the valve button 70A and the valve stem 82A upon pivoting of the actuators 50A and 50A'. The actuators 50A and 50A' are integrally connected to the undercap 30A through the hinge 60A integrally molded as a one-piece plastic unit with the undercap 30A.

The aerosol dispensing device 10A operates in the following manner. An operator grasps the gripping area 36A of the undercap 30A with one hand with the thumb or a finger of the operator placed on one of the actuators 50A and 50A'. The thumb or the finger of the operator squeezes one of the actuators 50A and 50A' inwardly as shown in FIGS. 11–18. The actuator 50A and 50A' move the valve button 70A and the valve stem 82A for discharging the aerosol product 14 from the valve stem 82A in a generally downward direction into the other hand of the operator.

In the alternative, the operator grasps the gripping area 36A of the undercap 30A with one hand with the thumb and one finger of the operator placed on the actuators 50A and 50A'. The thumb and the finger of the operator squeeze both actuators 50A and 50A' inwardly. The actuators 50A and 50A' move the valve button 70A and the valve stem 82A for discharging the aerosol product 14 from the valve stem 82A in a generally downward direction into the other hand of the operator. The operator squeezing both actuators 50A and 50A' inwardly enables the operator to dispense the aerosol product 14 with less effort than a non-aerosol dispenser. In the alternative, the plural actuators 50A and 50A' may be larger relative to FIGS. 1–18 for providing an easier actuation for the operator.

FIGS. 19 and 20 are front and side isometric views of a second embodiment of an aerosol dispensing device 10B for dispensing an aerosol product 14 from an aerosol container 20B. The second embodiment of an aerosol dispensing device 10B is similar to the first embodiment of the aerosol dispensing device 10A with similar structural parts having similar reference numerals.

FIGS. 21 and 22 are sectional views of FIGS. 19 and 20 illustrating an undercap 30B secured to the aerosol container 20B by a mounting 40B. The undercap 30B includes an actuator 50B pivotably connected to the undercap 30B by a hinge 60B. The actuator 50B actuates a valve button 70B connected to an aerosol valve 80B mounted to the aerosol container 20B. The actuation of the aerosol valve 80B enables the aerosol product 14 to be dispensed under the pressure of the aerosol propellant 16 from the aerosol container 20B to be discharged from the valve button 70B.

FIGS. 21 and 22 illustrate the actuator 50B in an unattended condition. The container 20B is shown as a bullet shape container extending between a top portion 21B and a bottom portion 22B. The aerosol container 20B has a sidewall 23B defining a container rim 24B. The bottom portion 22B of the aerosol container 20B tapers radially inwardly into a neck 25B terminating in a bead 26B. A flange 28B extends radially outward about the neck 25B of the aerosol container 20B. The aerosol container 20B defines an axis of symmetry 29B. The bead 26B supports an aerosol mounting cup 90B for sealably securing the aerosol valve 80B to the aerosol container 20B.

Figure 23:
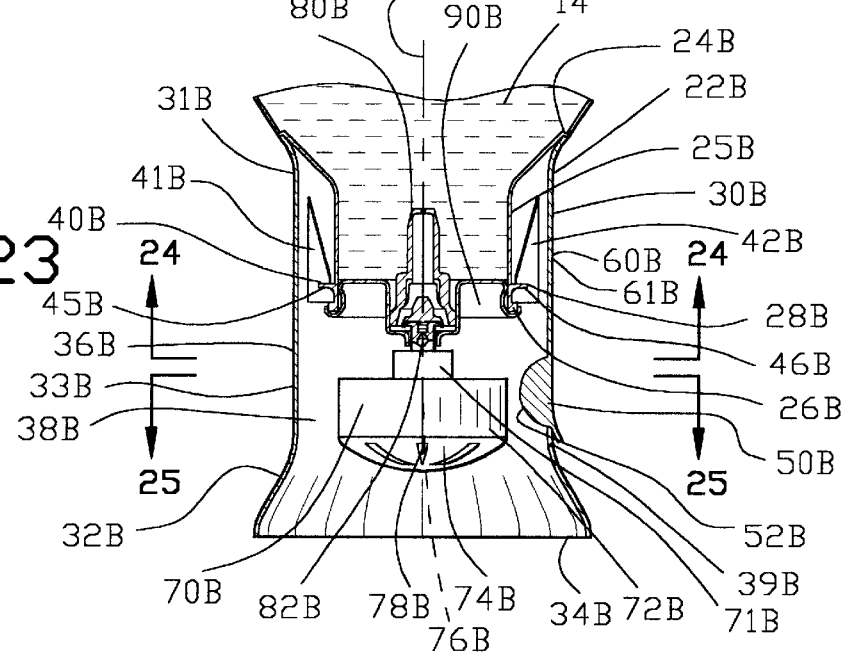
FIG. 23 is an enlarged view of a portion of FIG. 21.
Figure 25:
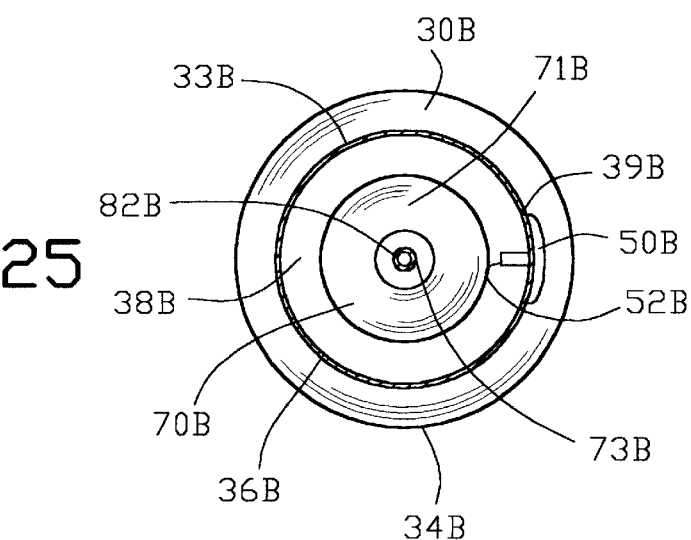
FIG. 25 is a sectional view along line 25—25 in FIG. 23.
Figure 27:
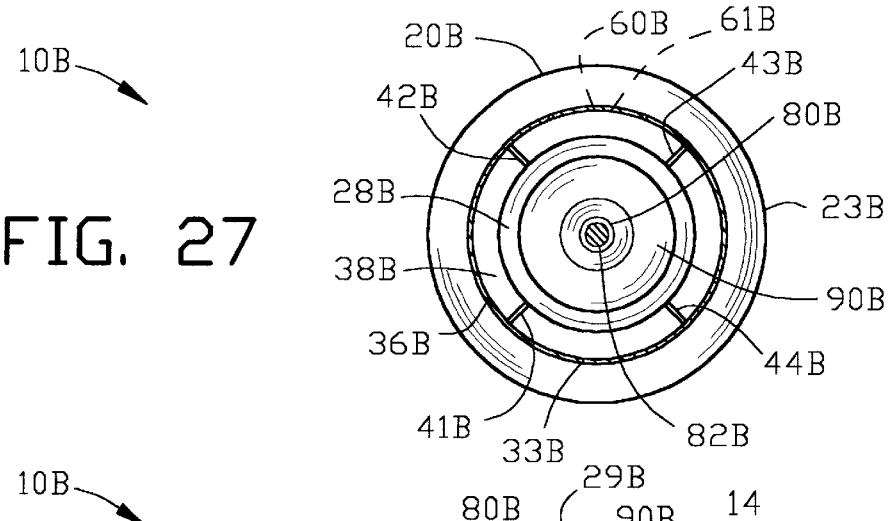
FIG. 27 is a sectional view along line 27—27 in FIG. 26.
Figure 26:
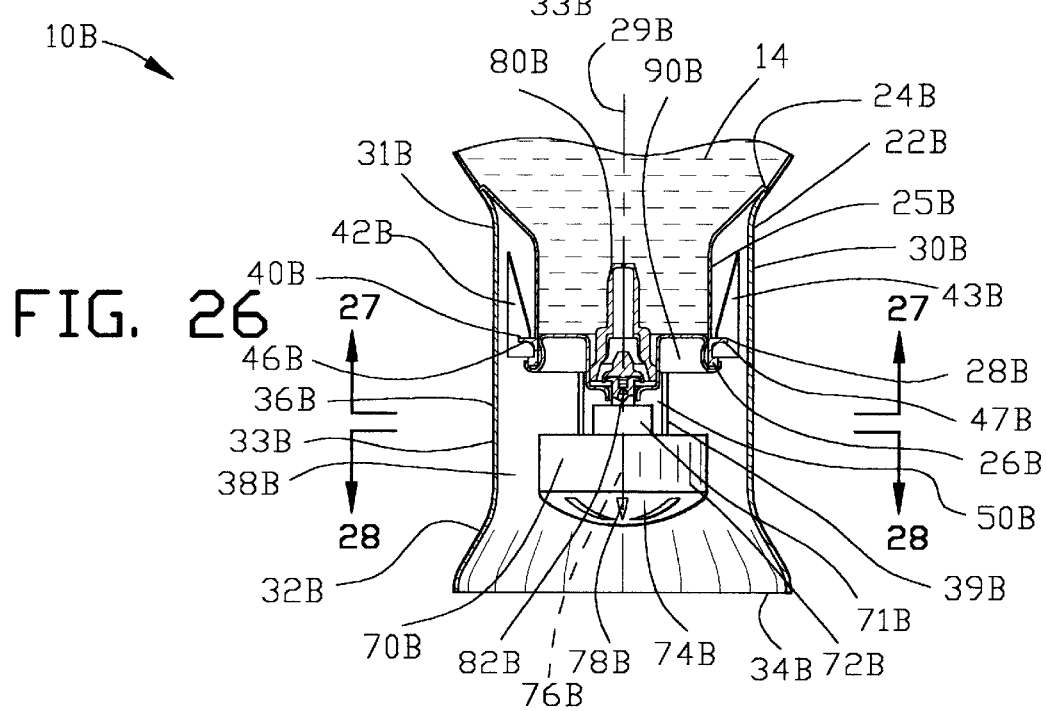
FIG. 26 is an enlarged view of a portion of FIG. 22.
Figure 28:
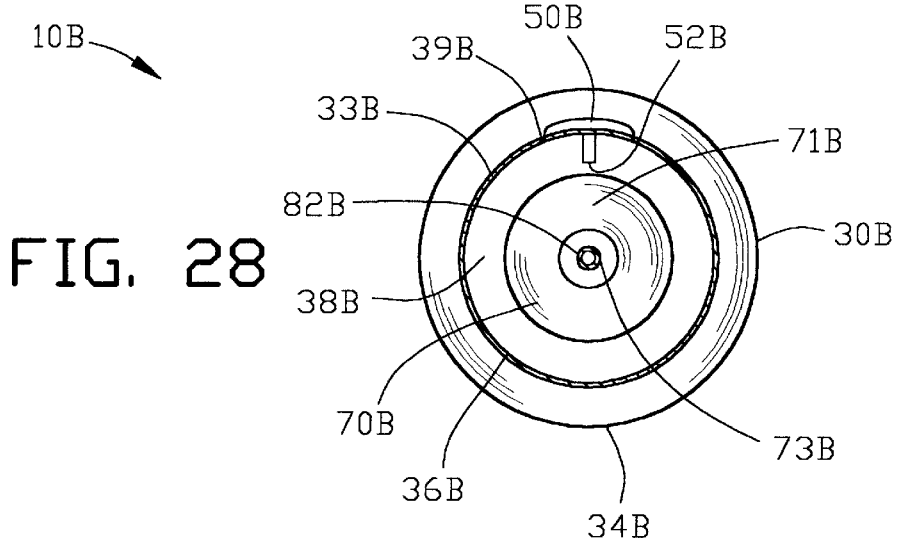
FIG. 28 is a sectional view along line 28—28 in FIG. 26.
Figure 32:
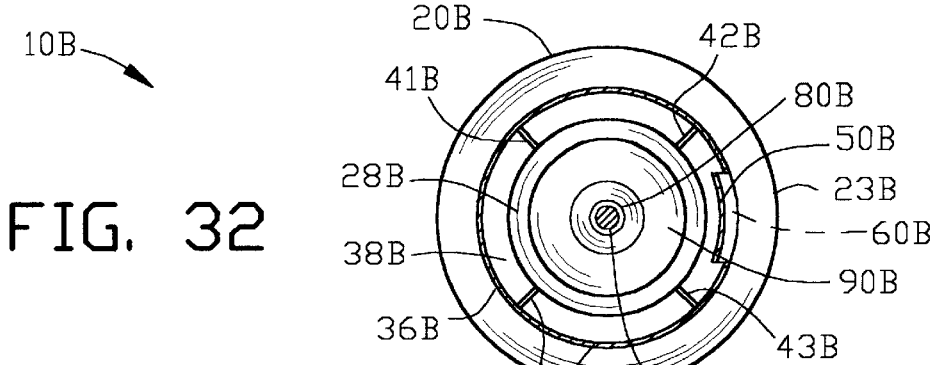
FIG. 32 is a sectional view along line 32—32 in FIG. 31.
Figure 31:
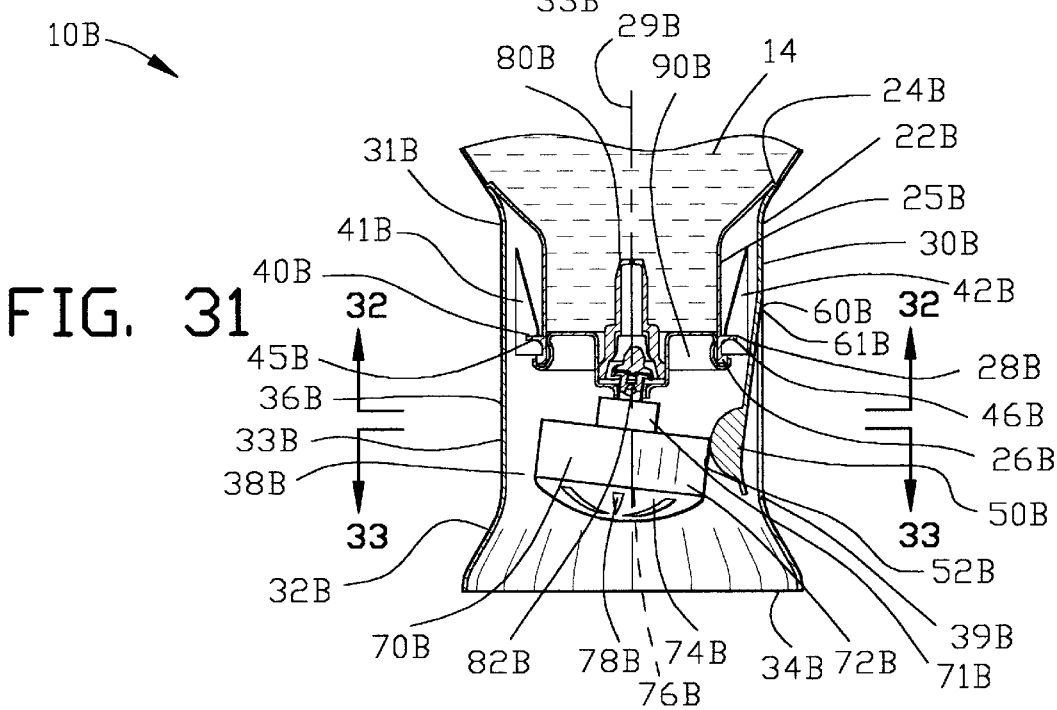
FIG. 31 is an enlarged view of a portion of FIG. 29.
Figure 33:
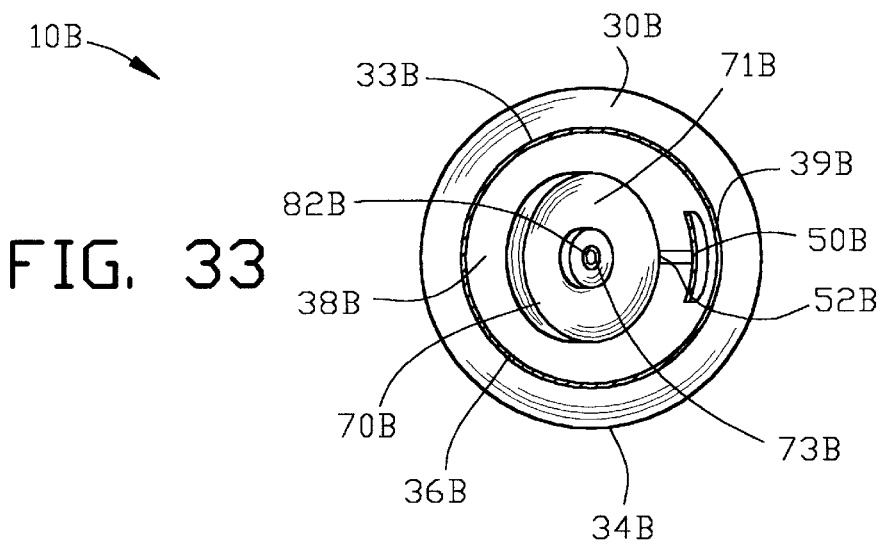
FIG. 33 is a sectional view along line 33—33 in FIG. 31.
Figure 42:
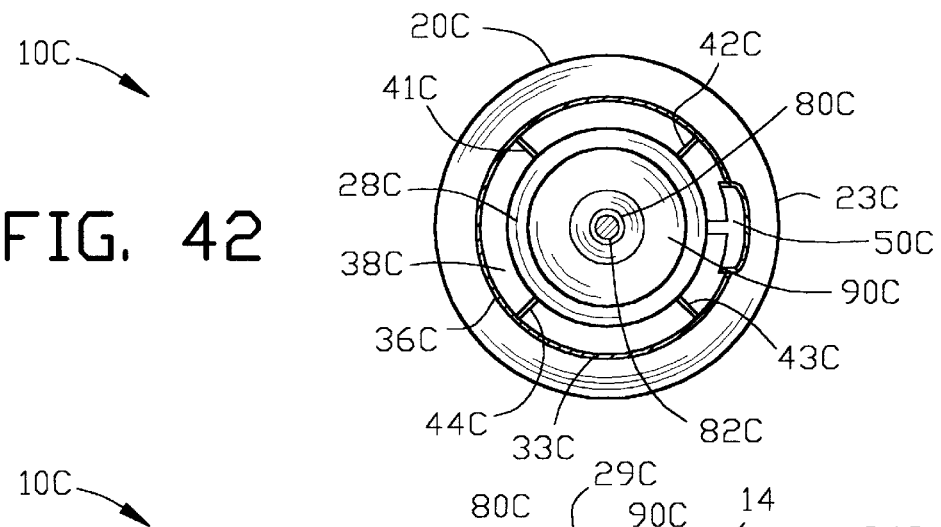
FIG. 42 is a sectional view along line 42—42 in FIG. 41.
Figure 41:
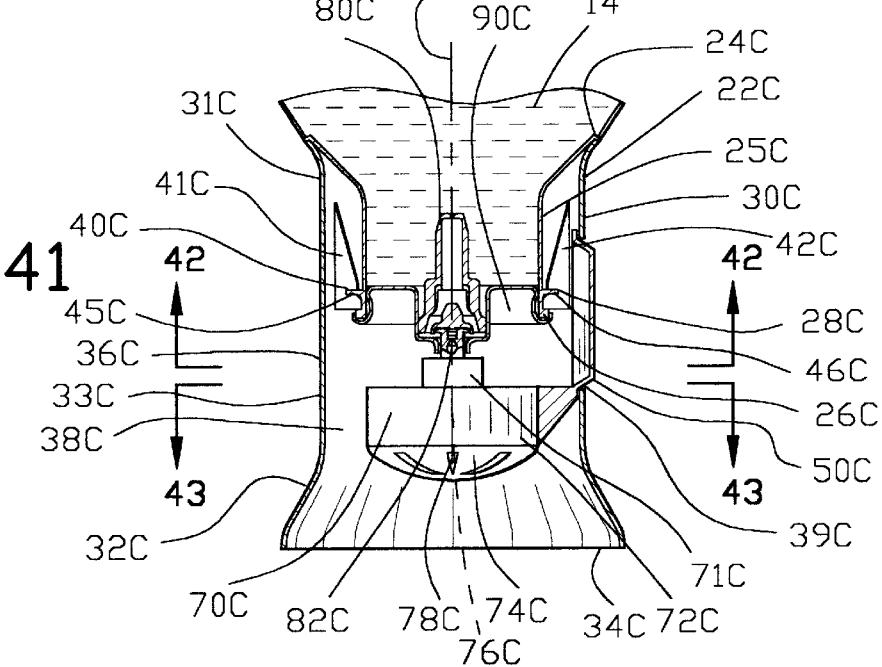
FIG. 41 is an enlarged view of a portion of FIG. 39.
Figure 43:
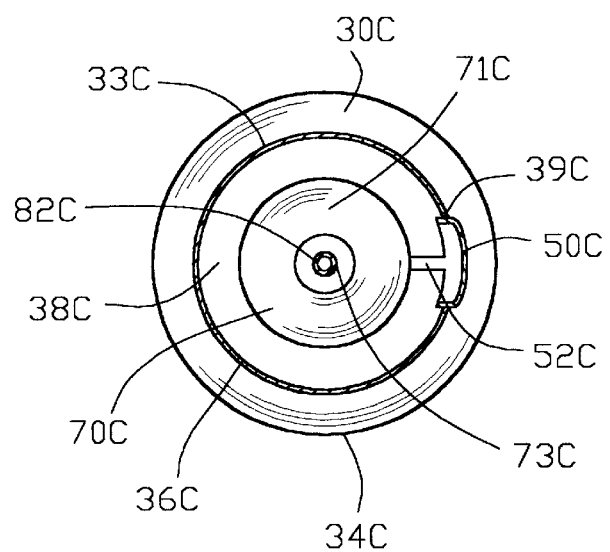
FIG. 43 is a sectional view along line 43—43 in FIG. 41.
Figure 45:
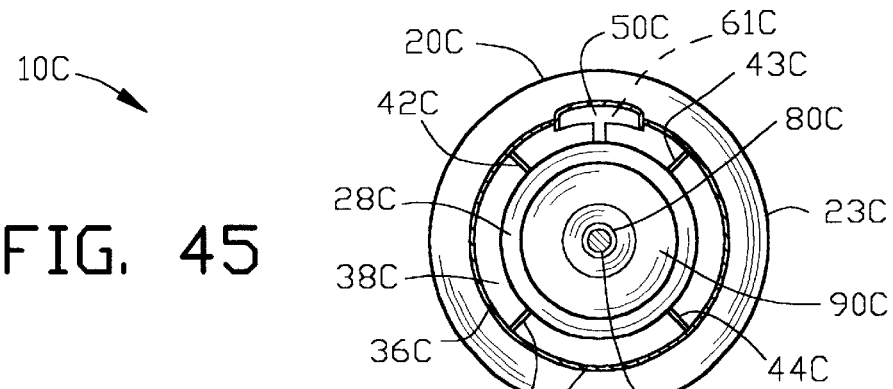
FIG. 45 is a sectional view along line 45—45 in FIG. 44.
Figure 44:
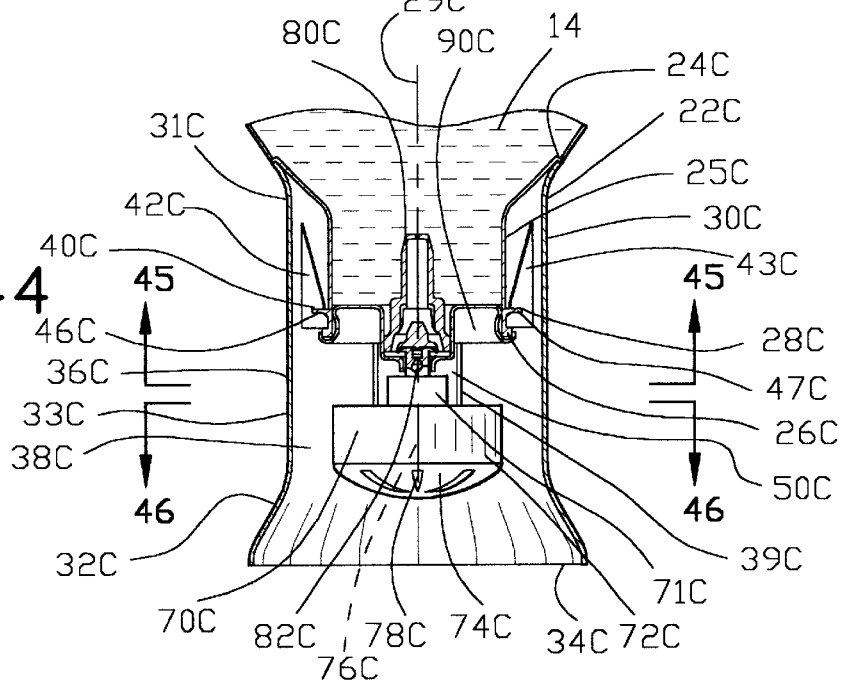
FIG. 44 is an enlarged view of a portion of FIG. 40.
Figure 46:
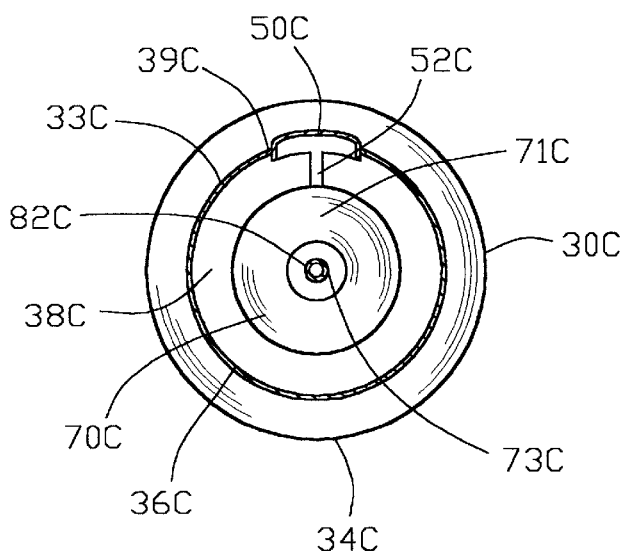
FIG. 46 is a sectional view along line 46—46 in FIG. 44.
Figure 50:
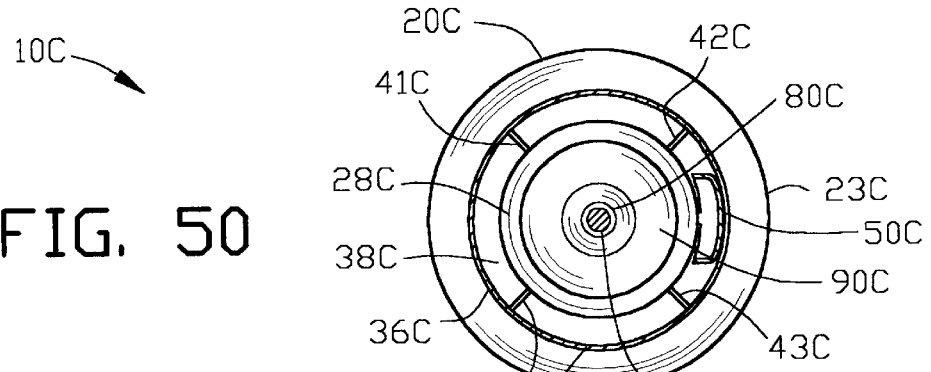
FIG. 50 is a sectional view along line 50—50 in FIG. 49.
Figure 49:
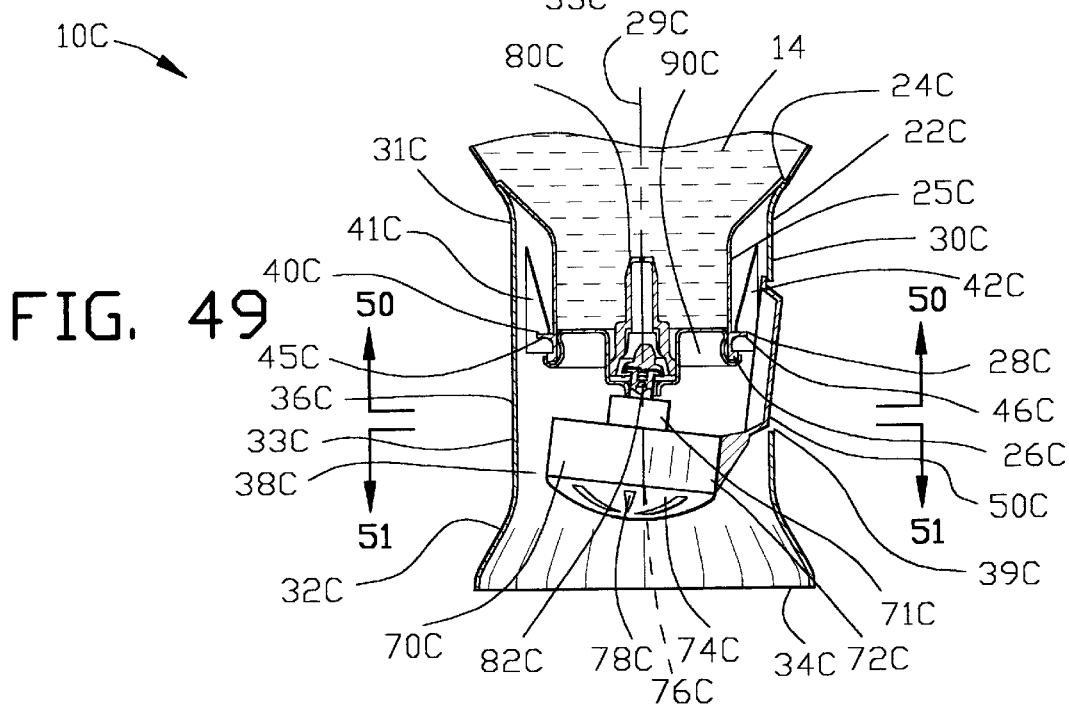
FIG. 49 is an enlarged view of a portion of FIG. 47.
Figure 51:
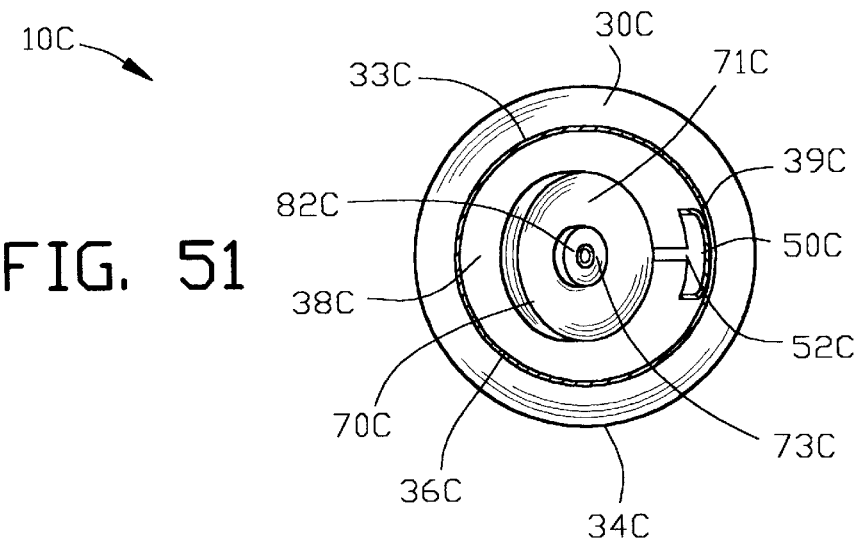
FIG. 51 is a sectional view along line 51—51 in FIG. 49.
Figure 53:
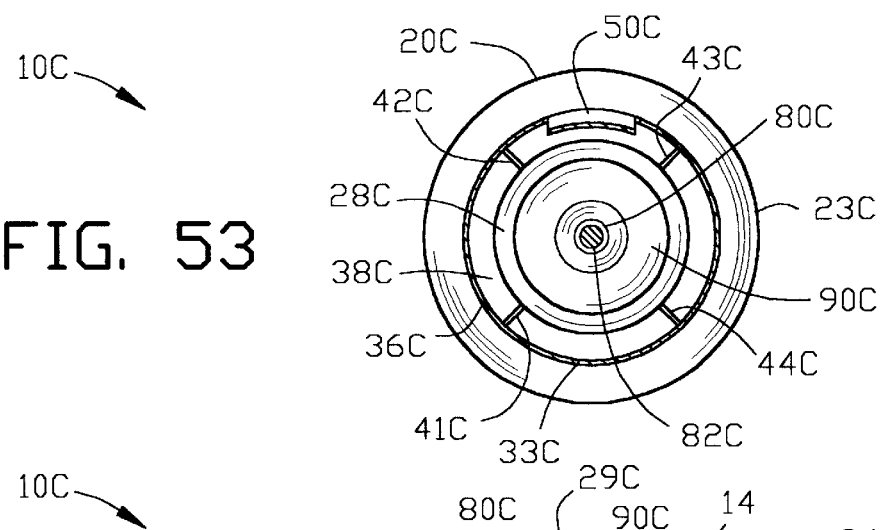
FIG. 53 is a sectional view along line 53—53 in FIG. 52.
Figure 52:
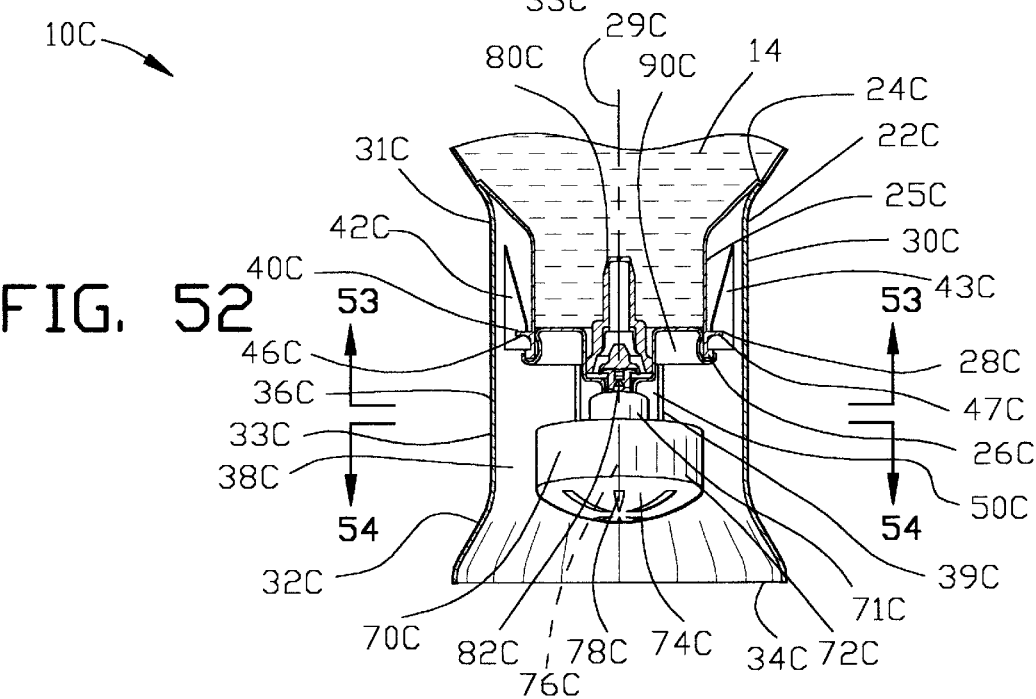
FIG. 52 is an enlarged view of a portion of FIG. 48.
Figure 54:
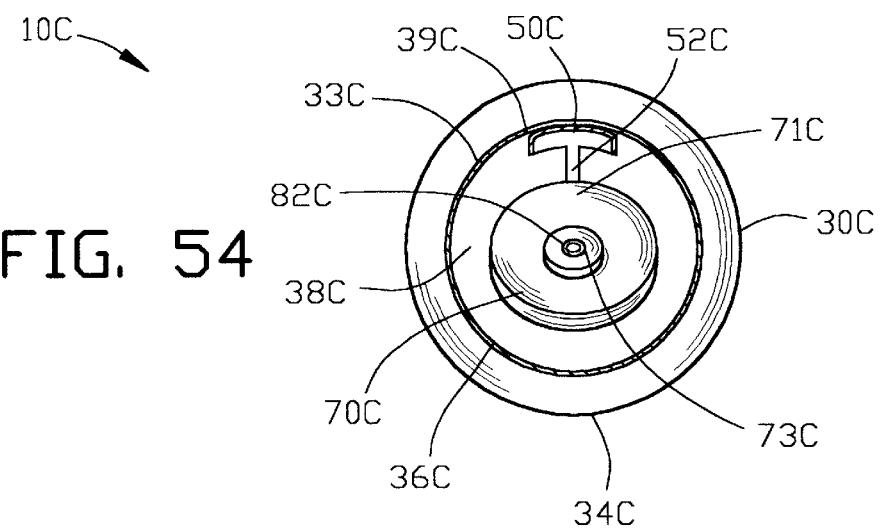
FIG. 54 is a sectional view along line 54—54 in FIG. 52.
Figure 60:
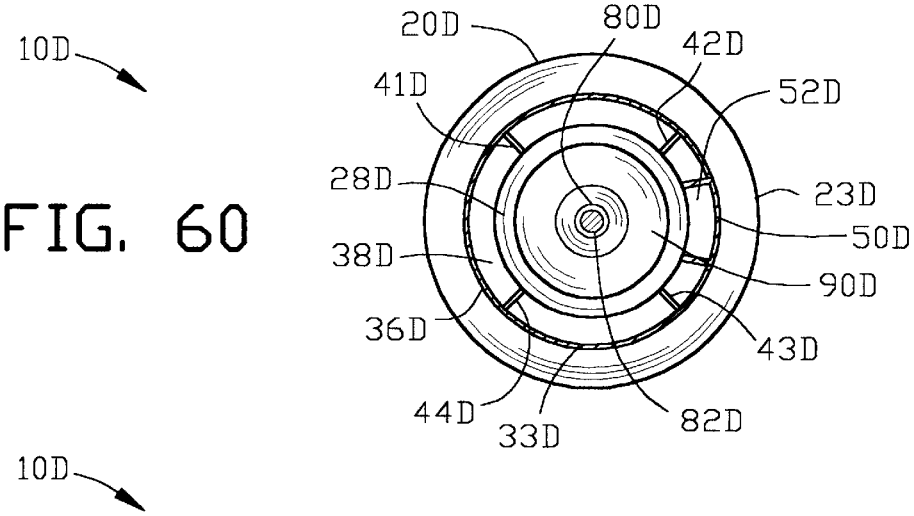
FIG. 60 is a sectional view along line 60—60 in FIG. 59.
Figure 59:
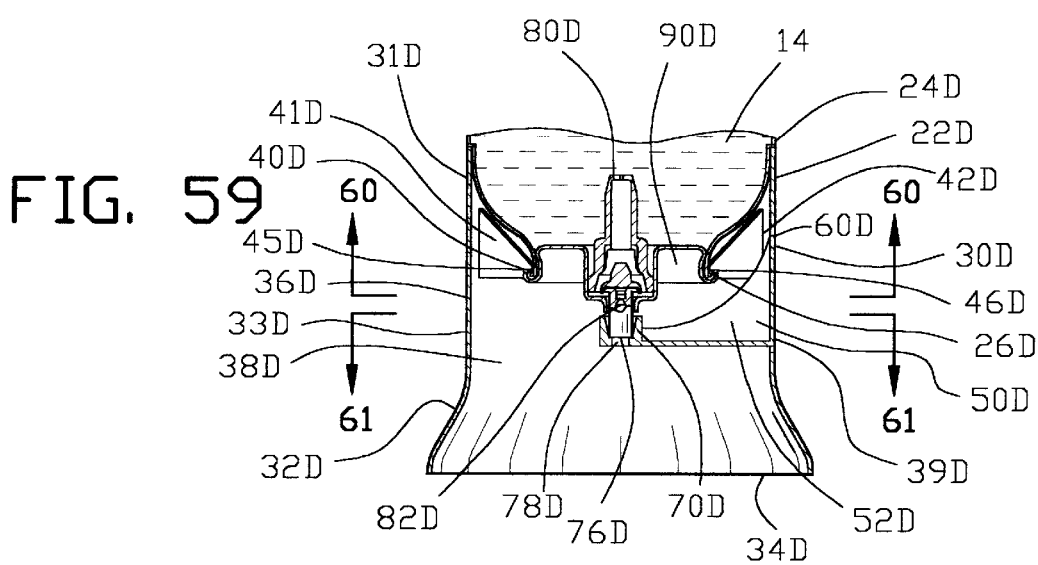
FIG. 59 is an enlarged view of a portion of FIG. 57.
Figure 61:
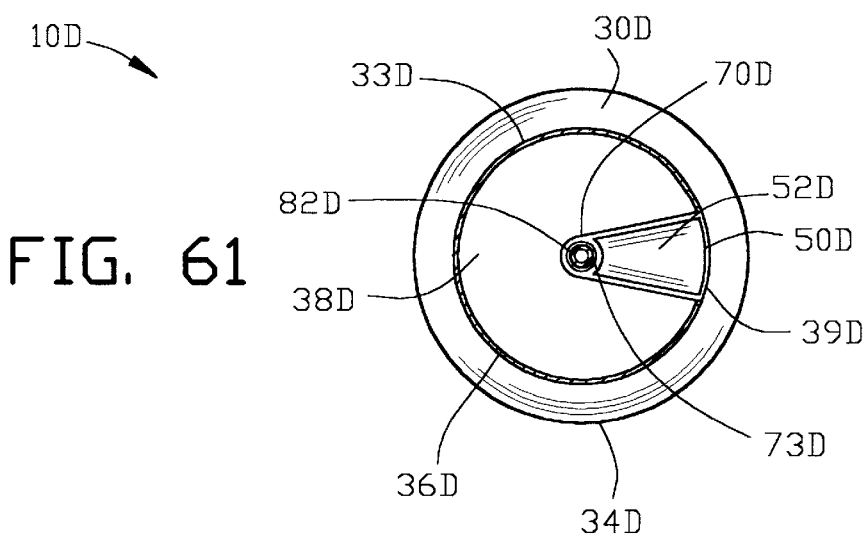
FIG. 61 is a sectional view along line 61—61 in FIG. 59.
Figure 63:
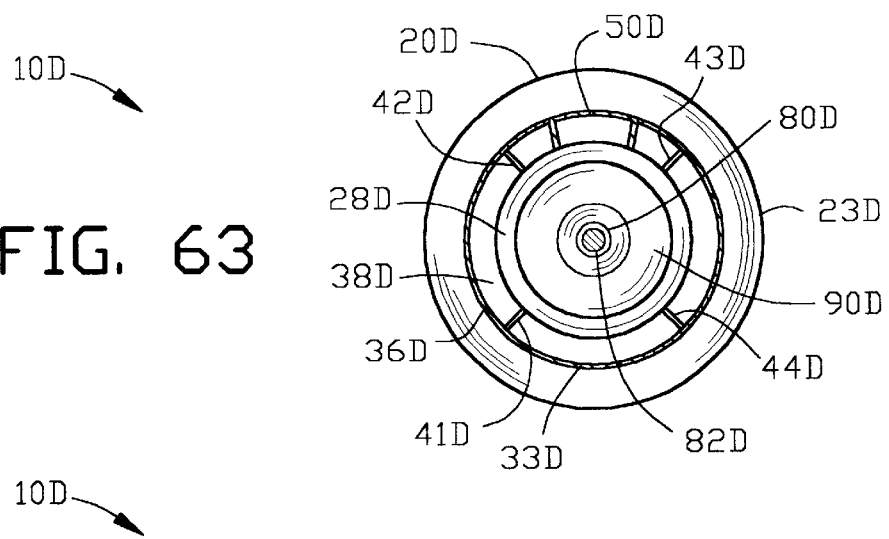
FIG. 63 is a sectional view along line 63—63 in FIG. 62.
Figure 62:
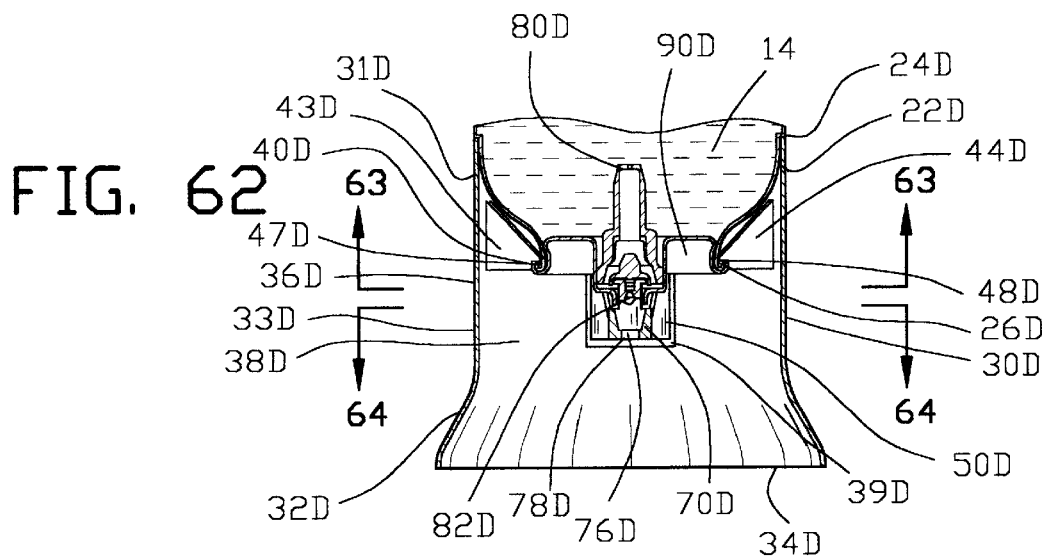
FIG. 62 is an enlarged view of a portion of FIG. 58.
Figure 64:
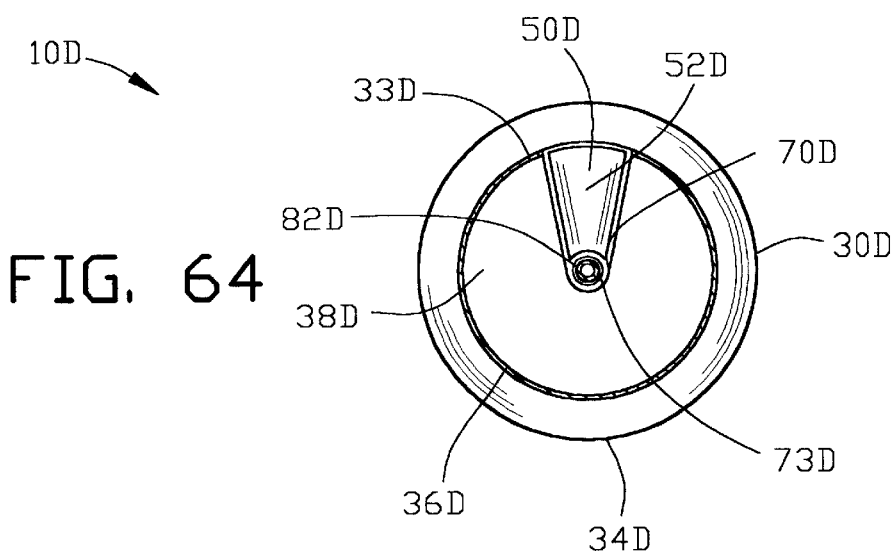
FIG. 64 is a sectional view along line 64—64 in FIG. 62.
Figure 68:
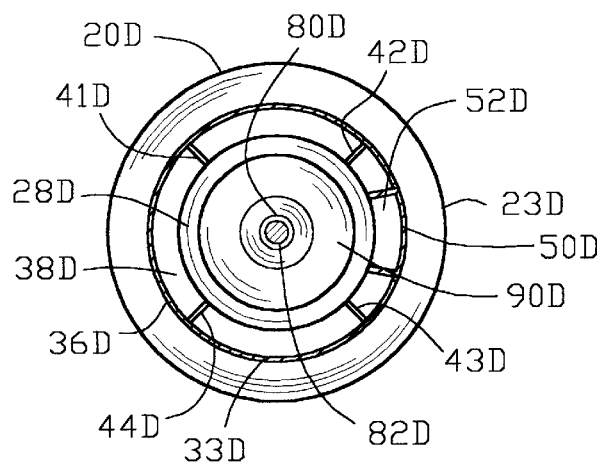
FIG. 68 is a sectional view along line 68—68 in FIG. 65.
Figure 67:
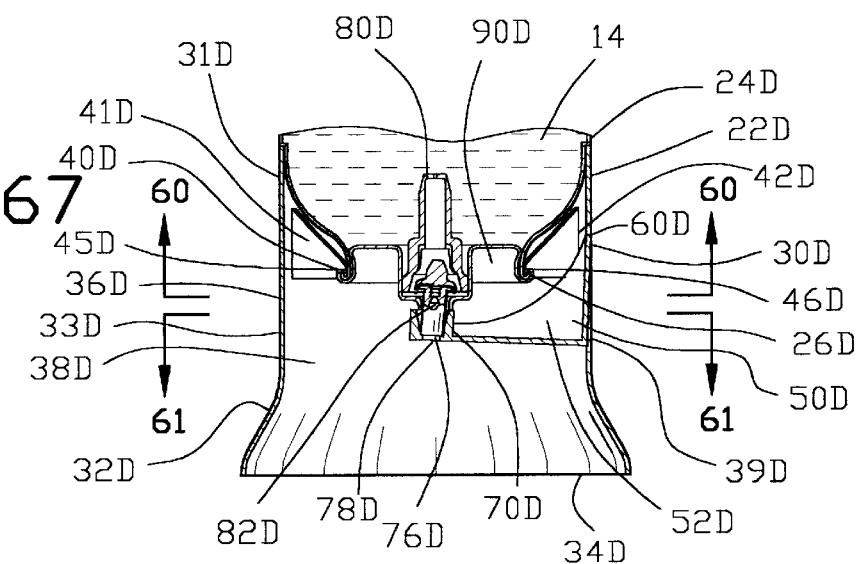
FIG. 67 is an enlarged view of a portion of FIG. 65.
Figure 69:
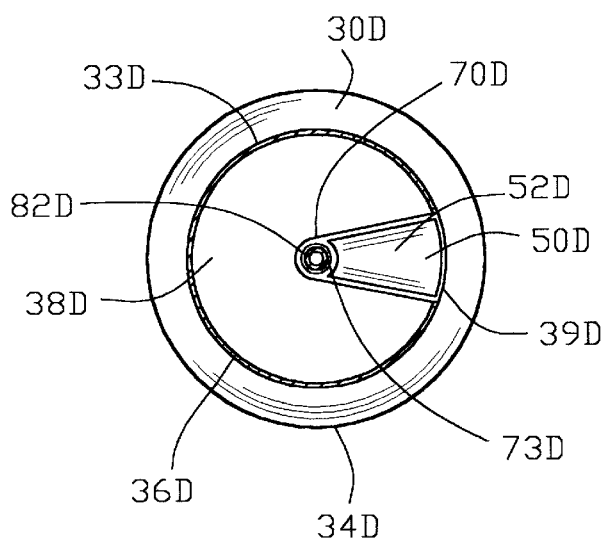
FIG. 69 is a sectional view along line 69—69 in FIG. 65.
Figure 71:
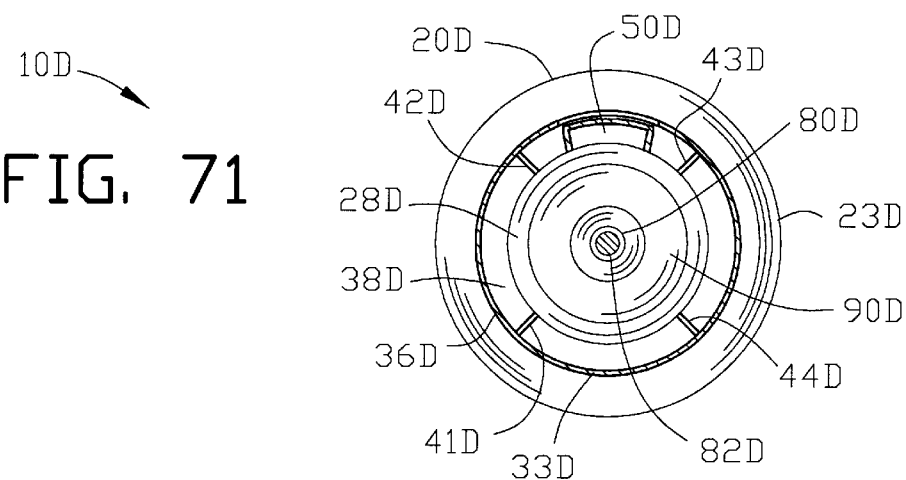
FIG. 71 is a sectional view along line 71—71 in FIG. 70.
Figure 70:
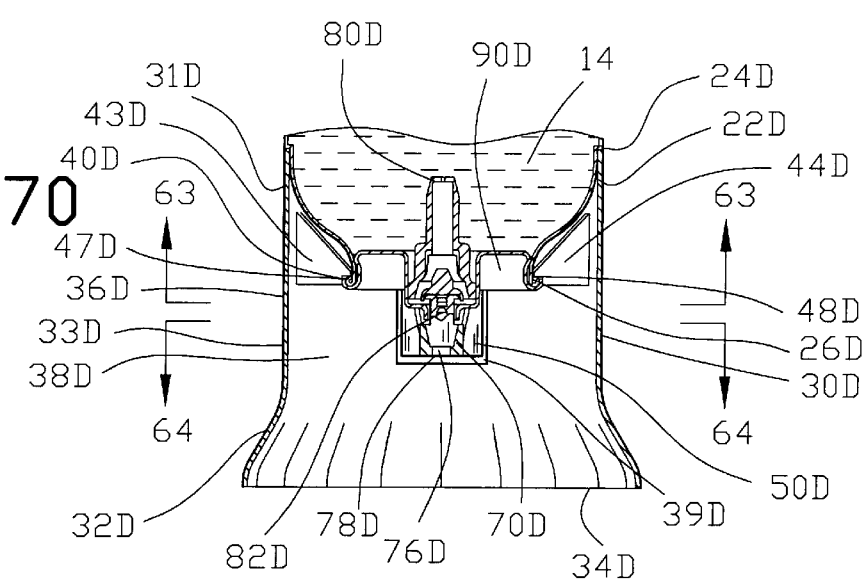
FIG. 70 is an enlarged view of a portion of FIG. 66.
Figure 72:
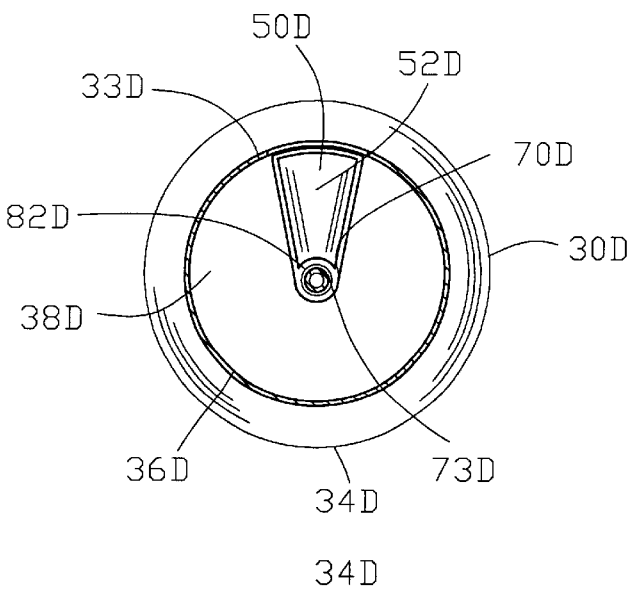
FIG. 72 is a sectional view along line 72—72 in FIG. 70.

FIGS. 23–25 and 26–28 are enlarged views of portions of FIGS. 21 and 23 respectively. The undercap 30B has a top portion 31B and a bottom portion 32B with a sidewall 33B extending therebetween. The undercap 30B includes an enlarged base 34B. Preferably, the undercap 30B is formed from a unitary and resilient polymeric material.

The undercap 30B includes a gripping area 36B having a cylindrically-shaped cross-section. The undercap 30B comprises a plastic shell defining an undercap aperture 38B for providing a passage for dispensing the aerosol product 14 in a generally downward direction through the undercap 30B.

The undercap 30B is secured to the aerosol container 20B by a mounting 40B. The mounting 40B comprises a plurality of ribs 41B–44B extending inwardly from the sidewall 33B. The plurality of ribs 41B–44B have recesses 45B–48B for engaging with the flange 28B to secure the undercap 30B to the aerosol container 20B in a snap locking engagement. The top portion 31B of the undercap 30B is received within the container rim 24B of the aerosol container 20B.

The actuator 50B is located in the sidewall orifice 39B of the sidewall 33B of the undercap 30B for actuating the aerosol valve 80B. The actuator 50B pivots about a hinge 60B having a hinge axis 61B. The hinge axis 61B is substantially perpendicular to the axis of symmetry 29B extending through the aerosol container 20B. The actuator 50B and the hinge 60B are integrally connected to the undercap 30B. The actuator 50B is integrally connected to the undercap 30B through the hinge 60B. The actuator 50B pivots on hinge 60B to extend into the sidewall orifice 39B. Preferably, the actuator 50B and the hinge 60B are molded as a one-piece plastic unit with the undercap 30B.

The aerosol valve 80B is secured into the aerosol mounting cup 90B in a conventional fashion. The aerosol mounting cup 90B is sealed to the bead 26B of the container 20B. The valve button 70B is secured to the valve stem 82B as set forth previously.

FIGS. 29 and 30 are sectional views similar to FIGS. 21 and 22 illustrating the actuator 50B in an actuated condition. When the valve stem 82B is displaced into the open position as shown in FIGS. 29 and 30, the aerosol dispensing device 10B dispenses the aerosol product 14 under the pressure of the aerosol propellant 16 in a generally downward direction through the undercap 30B from the valve button 70B.

FIGS. 31–33 and 34–36 are enlarged views of portions of FIGS. 29 and 30 respectively. The aerosol valve 80B is shown as a tilt valve but it should be understood that the invention may be modified to function with a vertical action valve.

The actuator 50B is movably mounted relative to the undercap 30B for moving the valve button 70B and the valve stem 82B upon displacement of the actuator 50B. The displacement of the actuator 50B moves the aerosol valve 80B into the open position to dispense the aerosol product 14 under the pressure of the aerosol propellant 16 in a generally downward direction through the undercap 30B.

The actuator 50B includes an actuator surface 52B extending radially inwardly from the actuator 50B. The actuator surface 52B engages the valve button 70B upon an inward movement of the actuator 50B. The displacement of the actuator 50B moves the actuator surface 52B into engagement with the valve button 70B to displace the aerosol valve 80B into the open position to dispense the aerosol product 14 under the pressure of the aerosol propellant 16.

In contrast to FIGS. 1–18, the actuator 50B in FIGS. 19–36 is pivotably mounted on the undercap 30B about a hinge axis 61B substantially perpendicular to the axis of cylindrical symmetry 29B extending through the aerosol container 20B. The actuator 50B is oriented for enabling the operator to pivot the actuator 50B by a pulling or trigger motion rather than a gripping or squeezing motion as shown in FIGS. 1–18. The fingers of the operator pulls the actuator 50B inwardly as shown in FIGS. 29–36. The actuator 50B moves the valve button 70B and the valve stem 82B for discharging the aerosol product 14 from the valve stem 82B in a generally downward direction into the other hand of the operator.

FIGS. 37 and 38 are front and side isometric views of a third embodiment of an aerosol dispensing device 10C for dispensing an aerosol product 14 from an aerosol container 20C. The third embodiment of an aerosol dispensing device 10C is similar to the first embodiment of the aerosol dispensing device 10A with similar structural parts having similar reference numerals.

FIGS. 39 and 40 are sectional views of FIGS. 37 and 38 illustrating an undercap 30C secured to the aerosol container 20C by a mounting 40C. The undercap 30C includes an actuator 50C for actuating a valve button 70C. The actuator 50C actuates the valve button 70C connected to an aerosol valve 80C mounted to the aerosol container 20C. The actuation of the aerosol valve 80C enables the aerosol product 14 to be dispensed under the pressure of the aerosol propellant 16 from the aerosol container 20C and to be discharged from the valve button 70C.

FIGS. 39 and 40 illustrate the actuator 50C in an unattended condition. The container 20C is shown as a bullet shape container extending between a top portion 21C and a bottom portion 22C. The aerosol container 20C has a sidewall 23C defining a container rim 24C. The bottom portion 22C of the aerosol container 20C tapers radially inwardly into a neck 25C terminating in a bead 26C. A flange 28C extends radially outward about the neck 25C of the aerosol container 20C. The aerosol container 20C defines an axis of symmetry 29C. The bead 26C supports an aerosol mounting cup 90C for sealably securing the aerosol valve 80C to the aerosol container 20C.

FIGS. 41–43 and 44–46 are enlarged views of portions of FIGS. 39 and 40 respectively. The undercap 30C has a top portion 31C, a bottom portion 32C, a sidewall 33C and an enlarged base 34C. The undercap 30C includes a gripping area 36C having a cylindrically-shaped cross-section. The undercap 30C comprises a plastic shell defining an undercap aperture 38C for providing a passage for dispensing the aerosol product 14 in a generally downward direction through the undercap 30C. A sidewall orifice 39C is defined in the sidewall 33C of the undercap 30C.

The undercap 30C is secured to the aerosol container 20C by a mounting 40C comprising a plurality of ribs 41C–44C extending inwardly from the sidewall 33C. The plurality of ribs 41C–44C have recesses 45C–48C for engaging with the flange 28C to secure the undercap 30C to the aerosol container 20C in a snap locking engagement. The top portion 31C of the undercap 30C is received within the container rim 24C of the aerosol container 20C.

The valve button 70C is secured to the valve stem 82C. A top portion 71C of the valve button 70C is provided with a socket 73C for frictionally receiving the valve stem 82C of the aerosol valve 80C. A bottom portion 72C of the valve button 70C defines a terminal orifice 78C.

The actuator 50C includes an actuator surface 52C interconnecting the actuator 50C to the valve button 70C. The actuator 50C may be integrally connected to the valve button 70C by the actuator surface 52C. Preferably, the actuator 50C and actuator surface 52C and the valve button 70C are molded as a one-piece plastic unit. When the valve button 70C is secured to the valve stem 82C of the aerosol valve 80C, the actuator 50C is positioned within the sidewall orifice 39C. The actuator 50C may be depressed into the sidewall orifice 39C of the sidewall 33C of the undercap 30C for actuating the aerosol valve 80C.

FIGS. 47 and 48 are sectional views similar to FIGS. 39 and 40 illustrating the actuator 50C in an actuated condition. When the valve stem 82C is displaced into the open position as shown in FIGS. 47 and 48, the aerosol dispensing device 10C dispenses the aerosol product 14 under the pressure of the aerosol propellant 16 in a generally downward direction through the undercap 30C from the valve button 70C.

FIGS. 49–51 and 52–54 are enlarged views of portions of FIGS. 47 and 48 respectively. The actuator 50C is secured to the valve button 70C. The actuator 50C is independent of the undercap 30C for moving the valve button 70C and the valve stem 82C upon displacement of the actuator 50C. The displacement of the actuator 50C into the sidewall orifice 39C moves the aerosol valve 80C into the open position to dispense the aerosol product 14 under the pressure of the aerosol propellant 16 in a generally downward direction through the undercap 30C.

In contrast to FIGS. 1–18 and FIGS. 19–36, the actuator 50C in FIGS. 37–54 is independent of the undercap 30C. The actuator 50C is secured to the valve button 70C. The actuator 50C is oriented for enabling the operator to depress the actuator 50C by a pulling or trigger motion. The fingers of the operator depress the actuator 50C inwardly as shown in FIGS. 47–54. The actuator 50C moves the valve button 70C and the valve stem 82C for discharging the aerosol product 14 from the valve stem 82C in a generally downward direction into the other hand of the operator.

FIGS. 55 and 56 are front and side isometric views of a fourth embodiment of an aerosol dispensing device 10D for dispensing an aerosol product 14 from an aerosol container 20D. The fourth embodiment of an aerosol dispensing device 10D is similar to the first embodiment of the aerosol dispensing device 10D with similar structural parts having similar reference numerals.

FIGS. 57 and 58 are sectional views of FIGS. 55 and 56 illustrating an undercap 30D secured to the aerosol container 20D by a mounting 40D. The undercap 30D includes an actuator 50D pivotably connected to the undercap 30D by a hinge 60D. The actuator 50D actuates a valve button 70D connected to an aerosol valve 80D mounted to the aerosol container 20D. The actuation of the aerosol valve 80D enables the aerosol product 14 to be dispensed under the pressure of the aerosol propellant 16 from the aerosol container 20D to be discharged from the valve button 70D.

FIGS. 57 and 58 illustrate the actuator 50D in an unattended condition. The container 20D is shown as a cylindrical shape container extending between a top portion 21D and a bottom portion 22D. The aerosol container 20D has a sidewall 23D defining a container rim 24D. The bottom portion 22D of the aerosol container 20D tapers radially inwardly terminating in a bead 26D. The aerosol container 20D defines an axis of symmetry 29D. The bead 26D supports an aerosol mounting cup 90D for sealably securing the aerosol valve 80D to the aerosol container 20D.

FIGS. 59–61 and 62–64 are enlarged views of portions of FIGS. 57 and 58 respectively. The undercap 30D has a top portion 31D, a bottom portion 32D, a sidewall 33D and an enlarged base 34D. The undercap 30D includes a gripping area 36D having a cylindrically-shaped cross-section. The undercap 30D comprises a plastic shell defining an undercap aperture 38D for providing a passage for dispensing the aerosol product 14 in a generally downward direction through the undercap 30D. A sidewall orifice 39D is defined in the sidewall 33D of the undercap 30D.

The undercap 30D is secured to the aerosol container 20D by a mounting 40D comprising a plurality of ribs 41D–44D extending inwardly from the sidewall 33D. The plurality of ribs 41D–44D have recesses 45D–48D for engaging with the aerosol mounting cup 90D to secure the undercap 30D to the aerosol container 20D in a snap locking engagement. The top portion 31D of the undercap 30D is received within the container rim 24D of the aerosol container 20D.

The valve button 70D is frictionally secured to the valve stem 82D. A top portion 71A of the valve button 70A is provided with a socket 73D for frictionally receiving the valve stem 82D of the aerosol valve 80D. A bottom portion 72D of the valve button 70D defines a terminal orifice 78C.

The actuator 50D is located in the sidewall orifice 39D of the sidewall 33D of the undercap 30D for actuating the aerosol valve 80D. The hinge axis 61D is substantially perpendicular to the axis of symmetry 29D extending through the aerosol container 20D. The actuator 50D is integrally connected to the undercap 30D through the hinge 60D. The actuator 50D pivots on hinge 60D to extend into the sidewall orifice 39D.

The actuator 50D includes an actuator surface 52D interconnecting the actuator 50D to the valve button 70D. The actuator 50D may be integrally connecting to the valve button 70D by the actuator surface 52D. Preferably, the undercap 30D and the hinge 60D and the actuator 50D and the actuator surface 52D and the valve button 70D are molded as a one-piece plastic unit. The actuator 50D may be depressed into the sidewall orifice 39D of the sidewall 33D of the undercap 30D for actuating the aerosol valve 80D.

FIGS. 65 and 66 are sectional views similar to FIGS. 57 and 58 illustrating the actuator 50D in an actuated condition. When the valve stem 82D is displaced into the open position as shown in FIGS. 65 and 66, the aerosol dispensing device 10D dispenses the aerosol product 14 under the pressure of the aerosol propellant 16 in a generally downward direction through the undercap 30D from the valve button 70D.

FIGS. 67–69 and 70–72 are enlarged views of portions of FIGS. 65 and 66 respectively. The actuator 50D is secured to the valve button 70D. The actuator 50D may be pivoted on the hinge 60D for moving the valve button 70D and the valve stem 82D upon displacement of the actuator 50D. The displacement of the actuator 50D into the sidewall orifice 39D moves the aerosol valve 80D into the open position to dispense the aerosol product 14 under the pressure of the aerosol propellant 16 in a generally downward direction through the undercap 30D.

In contrast to FIGS. 1–18 and FIGS. 19–36 and FIGS. 37–54, the actuator 50D in FIGS. 55–72 is integrally formed with both the undercap 30D and the valve button 70D. The actuator 50D is secured to the valve button 70D. The actuator 50D is oriented for enabling the operator to depress the actuator 50D by a pulling or trigger motion. The fingers of the operator depress the actuator 50D inwardly as shown in FIGS. 47–54. The actuator 50D moves the valve button 70D and the valve stem 82D for discharging the aerosol product 14 from the valve stem 82D in a generally downward direction into the other hand of the operator.

The present invention provides an inverted aerosol dispensing device which provides a significant advancement for the aerosol industry. The inverted aerosol dispensing device incorporates an undercap mounted to a bottom portion of the aerosol container for storing and dispensing aerosol products in an inverted position. The inverted aerosol dispensing device is suitable for dispensing viscous aerosol products in downward direction.

Although the invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:
1. An inverted aerosol dispensing device, comprising:
an aerosol container extending between a top portion and a bottom portion for containing an aerosol product and an aerosol propellant therein;
a tilt aerosol valve located at said bottom portion of said aerosol container;
said tilt aerosol valve having a valve stem for displacing said aerosol valve from a biased closed position to an open position upon a tilting of said valve stem to discharge the aerosol product from the valve stem;
an undercap having a sidewall extending between a top portion and a bottom portion;
a mounting for securing said undercap to said aerosol container with said top portion of said undercap being adjacent to said bottom portion of said container;
said bottom portion of said undercap terminating in a base surface for supporting said aerosol container on a supporting surface to store the aerosol dispensing device in an inverted position; and
an actuator located in said sidewall of said undercap and being movably mounted relative to said undercap for tilting said valve stem upon movement of said actuator for discharging the aerosol product from the valve stem in a generally downwardly direction.

2. An inverted aerosol dispensing device as set forth in claim 1, wherein said actuator is connected to said undercap through a hinge having a pivotal axis substantially parallel to an axis of symmetry extending through said aerosol container.

3. An inverted aerosol dispensing device as set forth in claim 1, wherein said actuator is connected to said undercap through a hinge having a pivotal axis substantially perpendicular to an axis of symmetry extending through said aerosol container.

4. An inverted aerosol dispensing device as set forth in claim 1, wherein said actuator is integrally connected to said undercap through an integral hinge.

5. An inverted aerosol dispensing device as set forth in claim 1, wherein said actuator is integrally connected to said undercap through a hinge integrally molded as a one-piece plastic unit with said undercap.

6. An inverted aerosol dispensing device as set forth in claim 1, wherein said actuator is independent of said undercap.

7. An inverted aerosol dispensing device as set forth in claim 1, wherein said undercap defines a sidewall orifice between said top portion and said bottom portion of said undercap; and
said actuator at least partially extending into said sidewall orifice for enabling said actuator to be moved relative to said undercap.

8. An inverted aerosol dispensing device, comprising:
an aerosol container extending between a top portion and a bottom portion for containing an aerosol product and an aerosol propellant therein;
a tilt aerosol valve located at said bottom portion of said aerosol container;
said tilt aerosol valve having a valve stem for displacing said aerosol valve from a biased closed position to an open position upon a tilting of said valve stem to discharge the aerosol product from the valve stem;
an undercap having a sidewall extending between a top portion and a bottom portion;

a mounting for securing said undercap to said aerosol container with said top portion of said undercap being adjacent to said bottom portion of said container;

said bottom portion of said undercap terminating in a base surface for supporting said aerosol container on a supporting surface to store the aerosol dispensing device in an inverted position;

a sidewall orifice located between said top portion and said bottom portion in of said sidewall of said undercap;

an actuator located in said sidewall orifice of said undercap; and said actuator being movably mounted relative to said undercap for tilting said valve stem upon movement of said actuator for discharging the aerosol product from the valve stem in a generally downwardly direction.

9. An inverted aerosol dispensing device as set forth in claim 8, including an aperture defined in said undercap; and said valve stem directing the aerosol product in a generally downward direction through said aperture defined in said undercap.

10. An inverted aerosol dispensing device as set forth in claim 8, including a valve button having a terminal orifice;

said valve button being secured to said valve stem; and said actuator moving said valve button upon displacement of said actuator for moving said valve stem to direct the aerosol product through the valve stem to be discharged from said terminal orifice of said valve button in a generally downward direction.

11. An inverted aerosol dispensing device as set forth in claim 8, including a valve button having a terminal orifice and being secured to said valve stem; and said actuator being secured to said valve button for moving said valve stem to direct the aerosol product through the valve stem to be discharged from said terminal orifice of said valve button in a generally downward direction.

12. An inverted aerosol dispensing device as set forth in claim 8, including a valve button secured to said valve stem; and said actuator being integrally formed with said valve button for moving said valve stem to direct the aerosol product through the valve stem to be discharged from said terminal orifice of said valve button in a generally downward direction.

13. An inverted aerosol dispensing device as set forth in claim 8, including a valve button secured to said valve stem; and said actuator being connected to said undercap through a hinge; and said actuator being secured to said valve button.

14. An inverted aerosol dispensing device as set forth in claim 8, including a valve button secured to said valve stem; and said actuator being connected to said undercap through a hinge;

said actuator being secured to said valve button; and said undercap and said hinge and said actuator and said valve button being integrally molded as a one-piece plastic unit.

15. An inverted aerosol dispensing device, comprising:

an aerosol container for containing an aerosol product and an aerosol propellant therein;

said aerosol container defining a container axis extending between a top portion and a bottom portion of said aerosol container;

an aerosol valve located at said bottom portion of said aerosol container;

aerosol valve having a valve stem for displacing said aerosol valve from a biased closed position to an open position to discharge the aerosol product from the valve stem;

an undercap secured to the bottom portion of the aerosol container for supporting the aerosol container on a supporting surface; and an actuator pivotably mounted relative to said undercap about a hinge having a axis substantially parallel said container axis for moving said valve stem upon displacement of said actuator for discharging the aerosol product from the valve stem in a generally downwardly direction.

16. An inverted aerosol dispensing device as set forth in claim 15, wherein said actuator is integrally connected to said undercap through said hinge.

17. An inverted aerosol dispensing device as set forth in claim 15, wherein said actuator is integrally connected to said undercap through said hinge integrally molded as a one-piece plastic unit with said undercap.

18. An inverted aerosol dispensing device as set forth in claim 15, wherein said aerosol valve is a tilt valve wherein a tilting of said valve stem displaces said aerosol valve from said biased closed position to said open position.

19. An inverted aerosol dispensing device as set forth in claim 15, including a valve button having a terminal orifice;

said valve button being secured to said valve stem; and said actuator moving said valve button upon displacement of said actuator for moving said valve stem to direct the aerosol product through the valve stem to be discharged from said terminal orifice of said valve button in a generally downward direction.

20. An inverted aerosol dispensing device as set forth in claim 15, including an aperture defined in said undercap; and said valve stem directing the aerosol product in a generally downward direction through said aperture defined in said undercap.

21. An inverted aerosol dispensing device, comprising:

an aerosol container for containing an aerosol product and an aerosol propellant therein;

said aerosol container defining a container axis extending between a top portion and a bottom portion of said aerosol container;

a tilt aerosol valve located at said bottom portion of said aerosol container;

said tilt aerosol valve having a valve stem for displacing said aerosol valve from a biased closed position to an open position upon a tilting of said valve stem to discharge the aerosol product from the valve stem;

an undercap having a sidewall extending between a top portion and a bottom portion;

a mounting for securing said undercap to said aerosol container with said top portion of said undercap being adjacent to said bottom portion of said container;

said bottom portion of said undercap terminating in a base surface for supporting said aerosol container on a supporting surface to store the aerosol dispensing device in an inverted position;

an actuator located in said sidewall of said undercap and being pivotably mounted to said undercap about a hinge having a hinge axis substantially parallel said container axis for moving said valve stem upon displacement of said actuator for discharging the aerosol product from the valve stem in a generally downwardly direction; and said hinge axis being located adjacent to said top portion of said undercap and with said actuator being located adjacent to said bottom portion of said of said undercap.

22. An inverted aerosol dispensing device as set forth in claim 21, wherein said actuator is integrally connected to said undercap through said hinge.

23. An inverted aerosol dispensing device as set forth in claim 21, wherein said actuator is integrally connected to said undercap through said hinge integrally molded as a one-piece plastic unit with said undercap.

24. An inverted aerosol dispensing device as set forth in claim 21, including a valve button having a terminal orifice;

said valve button being secured to said valve stem; and said actuator moving said valve button upon displacement of said actuator for moving said valve stem to direct the aerosol product through the valve stem to be discharged from said terminal orifice of said valve button in a generally downward direction.

25. An inverted aerosol dispensing device as set forth in claim 21, including an aperture defined in said undercap; and said valve stem directing the aerosol product in a generally downward direction through said aperture defined in said undercap.

26. An inverted aerosol dispensing device, comprising:

an aerosol container extending between a top portion and a bottom portion for containing an aerosol product and an aerosol propellant therein;

aerosol valve located at said bottom portion of said aerosol container;

aerosol valve having a valve stem communicating with a terminal orifice of a valve button;

said valve button displacing said aerosol valve from a biased closed position to an open position to discharge the aerosol product from said terminal orifice of said valve button;

an undercap secured to the bottom portion of the aerosol container for supporting the aerosol container on a supporting surface in an inverted position;

an actuator movably mounted relative to said undercap for moving said valve button upon displacement of said actuator for discharging the aerosol product from said terminal orifice of said valve button in a generally downwardly direction; and said valve button being unitary with said actuator forming a one-piece structure and being independent of connection to said undercap.

27. An inverted aerosol dispensing device as set forth in claim 26, wherein said aerosol valve is a tilt valve wherein a tilting of said valve stem displaces said aerosol valve from said biased closed position to said open position.

28. An inverted aerosol dispensing device as set forth in claim 26, including an aperture defined in said undercap; and said valve stem directing the aerosol product in a generally downward direction through said aperture defined in said undercap.

29. An inverted aerosol dispensing device as set forth in claim 26, wherein said undercap has a sidewall extending between a top portion and a bottom portion with a sidewall orifice defined therebetween; and said actuator at least partially extending into said sidewall orifice for enabling said actuator to be moved relative to said undercap.

30. An inverted aerosol dispensing device, comprising:

an aerosol container extending between a top portion and a bottom portion for containing an aerosol product and an aerosol propellant therein;

aerosol valve located at said bottom portion of said aerosol container;

aerosol valve having a valve stem communicating with a terminal orifice of a valve button;

said valve button displacing said aerosol valve from a biased closed position to an open position to discharge the aerosol product from said terminal orifice of said valve button;

an undercap secured to the bottom portion of the aerosol container for supporting the aerosol container on a supporting surface in an inverted position;

an actuator movably connected to said undercap through an integral hinge for moving said valve button upon displacement of said actuator for discharging the aerosol product from said terminal orifice of said valve button in a generally downwardly direction; and said valve button being unitary with said actuator and with said undercap forming a one-piece structure.

31. An inverted aerosol dispensing device as set forth in claim 30, wherein said aerosol valve is a tilt valve wherein a tilting of said valve stem displaces said aerosol valve from said biased closed position to said open position.

32. An inverted aerosol dispensing device as set forth in claim 30, wherein said actuator is connected to said undercap through said hinge having a pivotal axis substantially parallel to an axis of symmetry extending through said aerosol container.

33. An inverted aerosol dispensing device as set forth in claim 30, wherein said actuator is connected to said undercap through said hinge having a pivotal axis substantially perpendicular to an axis of symmetry extending through said aerosol container.

34. An inverted aerosol dispensing device as set forth in claim 30, including an aperture defined in said undercap; and said valve stem directing the aerosol product in a generally downward direction through said aperture defined in said undercap.

* * * * *